US012757570B2

(12) United States Patent
Seo et al.

(10) Patent No.: US 12,757,570 B2
(45) Date of Patent: Oct. 6, 2026

(54) ORGANIC LIGHT EMITTING DIODE AND ORGANIC LIGHT EMITTING DISPLAY DEVICE INCLUDING THE SAME

(71) Applicant: LG Display Co., Ltd., Seoul (KR)

(72) Inventors: Jeong-Dae Seo, Paju-si (KR); Shin-Han Kim, Paju-si (KR); Min-Surk Hyung, Paju-si (KR); Kyu-Il Han, Paju-si (KR); Jin-Ho Park, Paju-si (KR); Seung-Kwang Roh, Paju-si (KR); Sun-Kap Kwon, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 962 days.

(21) Appl. No.: 17/981,171

(22) Filed: Nov. 4, 2022

(65) Prior Publication Data

US 2023/0209859 A1 Jun. 29, 2023

(30) Foreign Application Priority Data

Dec. 29, 2021 (KR) ........................ 10-2021-0191282

(51) Int. Cl.

| | |
|---|---|
| ***H01L 51/50*** | (2006.01) |
| ***C07D 471/14*** | (2006.01) |
| ***H10K 50/11*** | (2023.01) |
| ***H10K 50/16*** | (2023.01) |
| ***H10K 85/60*** | (2023.01) |
| *H10K 101/40* | (2023.01) |

(52) U.S. Cl.

CPC ........... *H10K 50/16* (2023.02); *C07D 471/14* (2013.01); *H10K 50/11* (2023.02); *H10K 85/654* (2023.02); *H10K 2101/40* (2023.02)

(58) Field of Classification Search

None

See application file for complete search history.

(56) References Cited

U.S. PATENT DOCUMENTS

2013/0264551 A1 10/2013 Pieh et al.
2016/0043327 A1 * 2/2016 Yoo ..................... H10K 85/655 257/40

(Continued)

FOREIGN PATENT DOCUMENTS

CN 105321984 A 2/2016
EP 3 667 755 A1 6/2020

(Continued)

*Primary Examiner* — Gregory D Clark

(74) *Attorney, Agent, or Firm* — Birch, Stewart, Kolasch & Birch, LLP

(57) ABSTRACT

An organic light emitting diode includes a first emitting part including a first emitting material layer (EML) and a first electron transporting layer (ETL), a second emitting part including a second EML and between the first emitting part and the second electrode, an n-type charge generation layer (CGL) contacting the first ETL and between the first ETL and the second emitting part, and a p-type CGL contacting the n-type CGL and between the n-type CGL and the second emitting part. The first ETL includes a first compound, and the n-type CGL includes a second compound and an n-type dopant. A lowest unoccupied molecular orbital (LUMO) energy level of the first compound can be higher than a LUMO energy level of the second compound.

18 Claims, 4 Drawing Sheets

(56) References Cited

U.S. PATENT DOCUMENTS

| | | | |
|---|---|---|---|
| 2016/0343776 | A1 | 11/2016 | Heo et al. |
| 2021/0074928 | A1 | 3/2021 | Yoo et al. |

FOREIGN PATENT DOCUMENTS

| | | | |
|---|---|---|---|
| KR | 10-2013-0113055 | A | 10/2013 |
| KR | 10-2016-0018332 | A | 2/2016 |
| KR | 10-2016-0137882 | A | 12/2016 |
| KR | 10-2021-0104788 | A | 8/2021 |

* cited by examiner

ORGANIC LIGHT EMITTING DIODE AND ORGANIC LIGHT EMITTING DISPLAY DEVICE INCLUDING THE SAME

CROSS-REFERENCE TO RELATED APPLICATIONS

The present application claims priority to Korean Patent Application No. 10-2021-0191282, filed in the Republic of Korea on Dec. 29, 2021, which is hereby incorporated by reference in its entirety into the present application.

BACKGROUND

Technical Field

The present disclosure relates to an organic light emitting diode, and more particularly, to an organic light emitting diode having a low driving voltage and an organic light emitting display device including the organic light emitting diode.

Discussion of the Related Art

A need for flat panel display devices having a small size is increased. Among the flat panel display devices, a technology of an organic light emitting display device, which includes an organic light emitting diode (OLED) and can be called an organic electroluminescent device, is being rapidly developed.

The OLED emits light by injecting electrons from a cathode as an electron injection electrode and holes from an anode as a hole injection electrode, both into an emitting material layer, combining the electrons with the holes, generating excitons, and transforming the excitons from an excited state to a ground state.

To provide high emitting efficiency, an OLED having a tandem structure including at least two emitting parts is introduced. However, the tandem structure OLED can have a limitation of high driving voltage.

SUMMARY OF THE DISCLOSURE

Accordingly, embodiments of the present disclosure are directed to an OLED and an organic light emitting display device that substantially obviate one or more of the problems associated with the limitations and disadvantages of the related art.

An object of the present disclosure is to provide an OLED and an organic light emitting device having a low driving voltage.

Additional features and aspects will be set forth in the description that follows, and in part will be apparent from the description, or can be learned by practice of the present disclosure concepts provided herein. Other features and aspects of the present disclosure concepts can be realized and attained by the structure particularly pointed out in the written description, or derivable therefrom, and the claims hereof as well as the appended drawings.

To achieve these and other advantages in accordance with the purpose of the embodiments of the present disclosure, as described herein, an aspect of the present disclosure is to provide an organic light emitting diode including a first electrode; a second electrode facing the first electrode; a first emitting part including a first emitting material layer and a first electron transporting layer and positioned between the first electrode and the second electrode; a second emitting part including a second emitting material layer and positioned between the first emitting part and the second electrode; an n-type charge generation layer contacting the first electron transporting layer and positioned between the first electron transporting layer and the second emitting part; and a p-type charge generation layer contacting the n-type charge generation layer and positioned between the n-type charge generation layer and the second emitting part, wherein the first electron transporting layer includes a first compound, and the n-type charge generation layer includes a second compound and an n-type dopant, and wherein a lowest unoccupied molecular orbital (LUMO) energy level of the first compound is higher than a LUMO energy level of the second compound, and a difference between the LUMO energy level of the first compound and the LUMO energy level of the second compound is 0.3 to 1.0 eV.

Another aspect of the present disclosure is to provide an organic light emitting display device including a substrate including a red pixel region, a green pixel region and a blue pixel region; and an organic light emitting diodes positioned over the substrate and corresponding to at least one of the red pixel region, the green pixel region and the blue pixel region. The organic light emitting diode can include: a first electrode; a second electrode facing the first electrode; a first emitting part including a first emitting material layer and a first electron transporting layer and positioned between the first electrode and the second electrode; a second emitting part including a second emitting material layer and positioned between the first emitting part and the second electrode; an n-type charge generation layer contacting the first electron transporting layer and positioned between the first electron transporting layer and the second emitting part; and a p-type charge generation layer contacting the n-type charge generation layer and positioned between the n-type charge generation layer and the second emitting part, wherein the first electron transporting layer includes a first compound, and the n-type charge generation layer includes a second compound and an n-type dopant, and wherein a LUMO energy level of the first compound is higher than a LUMO energy level of the second compound, and a difference between the LUMO energy level of the first compound and the LUMO energy level of the second compound is 0.3 to 1.0 eV.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the present disclosure and are incorporated in and constitute a part of this application, illustrate embodiments of the present disclosure and together with the description serve to explain principles of the present disclosure.

DETAILED DESCRIPTION OF THE EMBODIMENTS

Reference will now be made in detail to some of the examples and preferred embodiments, which are illustrated in the accompanying drawings. All the components of each display device according to all embodiments of the present disclosure are operatively coupled and configured.

Figure 1:
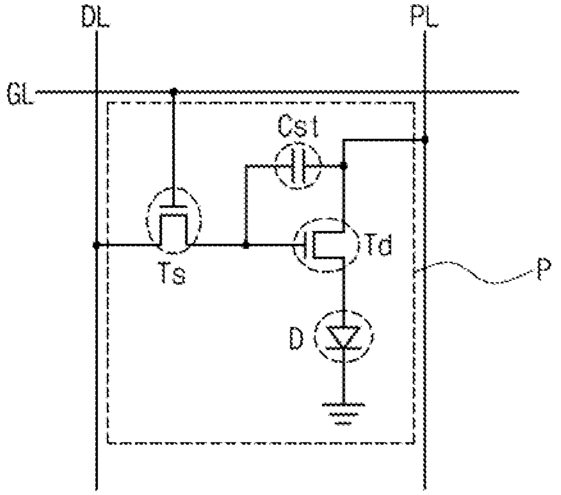
FIG. 1 is a schematic circuit diagram of an organic light emitting display device of the present disclosure.

FIG. 1 is a schematic circuit diagram of an organic light emitting display device of the present disclosure.

As shown in FIG. 1, an organic light emitting display device includes a gate line GL, a data line DL, a power line PL, a switching thin film transistor TFT Ts, a driving TFT Td, a storage capacitor Cst, and an OLED D. The gate line GL and the data line DL cross each other to define a pixel region P. The pixel region can include a red pixel region, a green pixel region and a blue pixel region.

The switching TFT Ts is connected to the gate line GL and the data line DL, and the driving TFT Td and the storage capacitor Cst are connected to the switching TFT Ts and the power line PL. The OLED D is connected to the driving TFT Td.

In the organic light emitting display device, when the switching TFT Ts is turned on by a gate signal applied through the gate line GL, a data signal from the data line DL is applied to the gate electrode of the driving TFT Td and an electrode of the storage capacitor Cst.

When the driving TFT Td is turned on by the data signal, an electric current is supplied to the OLED D from the power line PL. As a result, the OLED D emits light. In this case, when the driving TFT Td is turned on, a level of an electric current applied from the power line PL to the OLED D is determined such that the OLED D can produce a gray scale.

The storage capacitor Cst serves to maintain the voltage of the gate electrode of the driving TFT Td when the switching TFT Ts is turned off. Accordingly, even if the switching TFT Ts is turned off, a level of an electric current applied from the power line PL to the OLED D is maintained to next frame.

As a result, the organic light emitting display device displays a desired image.

Figure 2:
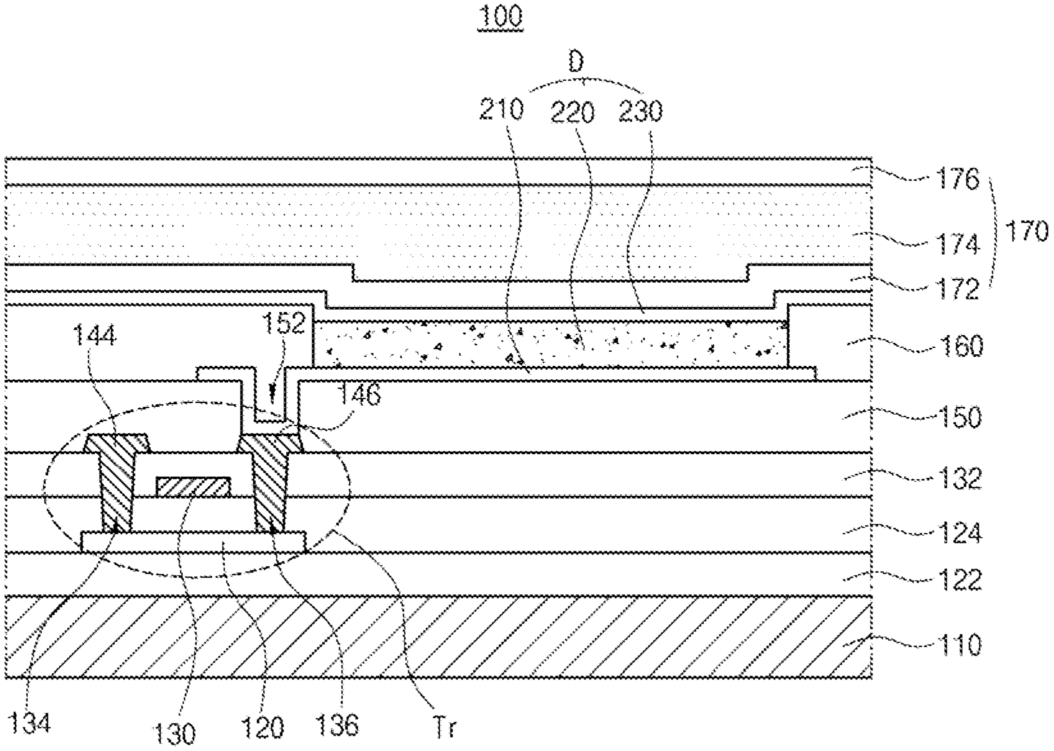
FIG. 2 is a schematic cross-sectional view of an organic light emitting display device according to a first embodiment of the present disclosure.

FIG. 2 is a schematic cross-sectional view of an organic light emitting display device according to a first embodiment of the present disclosure.

As shown in FIG. 2, the organic light emitting display device 100 includes a substrate 110, a TFT Tr on or over the substrate 110, a planarization layer 150 covering the TFT Tr and an OLED D on the planarization layer 150 and connected to the TFT Tr. A red pixel region, a green pixel region and a blue pixel region can be defined on the substrate 110.

The substrate 110 can be a glass substrate or a flexible substrate. For example, the flexible substrate can be one of a polyimide (PI) substrate, a polyethersulfone (PES) substrate, a polyethylenenaphthalate (PEN) substrate, a polyethylene terephthalate (PET) substrate and a polycarbonate (PC) substrate.

A buffer layer 122 is formed on the substrate, and the TFT Tr is formed on the buffer layer 122. The buffer layer 122 can be omitted. For example, the buffer layer 122 can be formed of an inorganic insulating material, e.g., silicon oxide or silicon nitride.

A semiconductor layer 120 is formed on the buffer layer 122. The semiconductor layer 120 can include an oxide semiconductor material or polycrystalline silicon.

When the semiconductor layer 120 includes the oxide semiconductor material, a light-shielding pattern can be formed under the semiconductor layer 120. The light to the semiconductor layer 120 is shielded or blocked by the light-shielding pattern such that thermal degradation of the semiconductor layer 120 can be prevented. On the other hand, when the semiconductor layer 120 includes polycrystalline silicon, impurities can be doped into both sides of the semiconductor layer 120.

A gate insulating layer 124 is formed on the semiconductor layer 120. The gate insulating layer 124 can be formed of an inorganic insulating material such as silicon oxide or silicon nitride.

A gate electrode 130, which is formed of a conductive material, e.g., metal, is formed on the gate insulating layer 124 to correspond to a center of the semiconductor layer 120. In FIG. 2, the gate insulating layer 124 is formed on an entire surface of the substrate 110. Alternatively, the gate insulating layer 124 can be patterned to have the same shape as the gate electrode 130.

An interlayer insulating layer 132 is formed on the gate electrode 130 and over an entire surface of the substrate 110. The interlayer insulating layer 132 can be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 120. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 144 and a drain electrode 146, which are formed of a conductive material, e.g., metal, are formed on the interlayer insulating layer 132.

The source electrode 144 and the drain electrode 146 are spaced apart from each other with respect to the gate electrode 130 and respectively contact both sides of the semiconductor layer 120 through the first and second contact holes 134 and 136.

The semiconductor layer 120, the gate electrode 130, the source electrode 144 and the drain electrode 146 constitute the TFT Tr. The TFT Tr serves as a driving element. Namely, the TFT Tr is the driving TFT Td (of FIG. 1).

In the TFT Tr, the gate electrode 130, the source electrode 144, and the drain electrode 146 are positioned over the semiconductor layer 120. Namely, the TFT Tr has a coplanar structure.

Alternatively, in the TFT Tr, the gate electrode can be positioned under the semiconductor layer, and the source and drain electrodes can be positioned over the semiconductor layer such that the TFT Tr can have an inverted staggered structure. In this instance, the semiconductor layer can include amorphous silicon.

The gate line and the data line cross each other to define the pixel region, and the switching TFT is formed to be connected to the gate and data lines. The switching TFT is connected to the TFT Tr as the driving element. In addition, the power line, which can be formed to be parallel to and spaced apart from one of the gate and data lines, and the storage capacitor for maintaining the voltage of the gate electrode of the TFT Tr in one frame can be further formed.

A planarization layer 150 is formed on an entire surface of the substrate 110 to cover the source and drain electrodes 144 and 146. The planarization layer 150 provides a flat top surface and has a drain contact hole 152 exposing the drain electrode 146 of the TFT Tr.

The OLED D is disposed on the planarization layer 150 and includes a first electrode 210, which is connected to the drain electrode 146 of the TFT Tr, an organic light emitting layer 220 and a second electrode 230. The organic light emitting layer 220 and the second electrode 230 are sequentially stacked on the first electrode 210. The OLED D is positioned in each of the red, green and blue pixel regions and respectively emits the red, green and blue light.

The first electrode 210 is separately formed in each pixel region. The first electrode 210 can be an anode and can include a transparent conductive oxide material layer, which can be formed of a conductive material, e.g., a transparent conductive oxide (TCO), having a relatively high work function, and a reflective layer. Namely, the first electrode 210 can be a reflective electrode.

For example, the transparent conductive oxide material layer can be formed of one of indium-tin-oxide (ITO), indium-zinc-oxide (IZO), indium-tin-zinc-oxide (ITZO), tin oxide (SnO), zinc oxide (ZnO), indium-copper-oxide (ICO) and aluminum-zinc-oxide (Al:ZnO, AZO), and the reflective layer can be formed of one of silver (Ag), an alloy of Ag and one of palladium (Pd), copper (Cu), indium (In) and neodymium (Nd), and aluminum-palladium-copper (APC) alloy. For example, the first electrode 210 can have a structure of ITO/Ag/ITO or ITO/APC/ITO.

In addition, a bank layer 160 is formed on the planarization layer 150 to cover an edge of the first electrode 210. Namely, the bank layer 160 is positioned at a boundary of the pixel region and exposes a center of the first electrode 210 in the pixel region.

The organic light emitting layer 220 is formed on the first electrode 210. The organic light emitting layer 220 includes a first emitting part including a first emitting material layer (EML) and a first electron transporting layer (ETL), a second emitting part including a second EML and a charge generation layer (CGL) including an n-type CGL and a p-type CGL and positioned between the first and second emitting parts.

A lowest unoccupied molecular orbital (LUMO) energy level of a first compound in the first ETL is higher than that of a host, e.g., a second compound, in the n-type CGL, and a difference between the LUMO energy level of the first compound in the first ETL and the LUMO energy level of the host in the n-type CGL can be 0.3 to 1.0 eV.

In addition, a LUMO energy level of a host, e.g., a third compound, in the p-type CGL is higher than that of the host in the n-type CGL, and a difference between the LUMO energy level of the host in the p-type CGL and the LUMO energy level of the host in the n-type CGL can be 1.0 to 2.0 eV.

Moreover, a LUMO energy level of a p-type dopant in the p-type CGL is higher than a highest occupied molecular orbital (HOMO) energy level of the host in the p-type CGL, and a difference between the LUMO energy level of the p-type dopant in the p-type CGL and the HOMO energy level of the host in the p-type CGL can be 0.1 to 0.5 eV.

The first compound in the first ETL and the host in the n-type CGL have the same core and different substituents.

The first emitting part can further include a hole blocking layer (HBL) being adjacent to and/or contacting the first ETL. In this instance, the HBL includes a fourth compound, and the fourth compound has the same core as the first compound of the first ETL.

The second electrode 230 is formed over the substrate 110 where the organic light emitting layer 220 is formed. The second electrode 230 covers an entire surface of the display area and can be formed of a conductive material having a relatively low work function to serve as a cathode. For example, the second electrode 230 can be formed of aluminum (Al), magnesium (Mg), calcium (Ca), silver (Ag) or their alloy, e.g., Mg—Ag alloy (MgAg). The second electrode 230 can have a thin profile, e.g., 10 to 30 nm, to be transparent (or semi-transparent).

Alternatively, in a bottom-emission type organic light emitting display device 100, the first electrode 210 can be a transparent electrode, and the second electrode 230 can be a reflective electrode. In this case, the first electrode 210 can have a single-layered structure of the transparent conductive oxide material layer.

The OLED D can further include a capping layer on the second electrode 230. The emitting efficiency of the OLED D can be further improved by the capping layer.

An encapsulation film (or an encapsulation layer) 170 is formed on the second electrode 230 to prevent penetration of moisture into the OLED D. The encapsulation film 170 includes a first inorganic insulating layer 172, an organic insulating layer 174 and a second inorganic insulating layer 176 sequentially stacked, but it is not limited thereto.

The organic light emitting display device 100 can include a color filter corresponding to the red, green and blue pixel regions. For example, the color filter can be positioned on or over the OLED D or the encapsulation film 170.

In addition, the organic light emitting display device 100 can further include a cover window on or over the encapsulation film 170 or the color filter. In this instance, the substrate 110 and the cover window have a flexible property such that a flexible organic light emitting display device can be provided.

Figure 3:
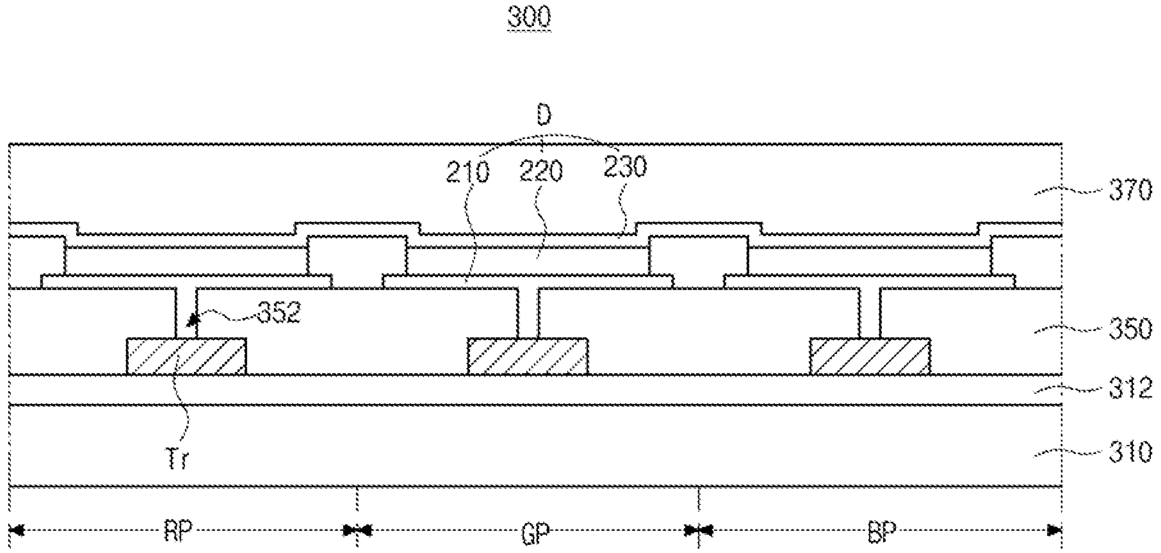
FIG. 3 is a schematic cross-sectional view of an organic light emitting display device according to a second embodiment of the present disclosure.

FIG. 3 is a schematic cross-sectional view of an organic light emitting display device according to a second embodiment of the present disclosure.

As shown in FIG. 3, the organic light emitting display device 300 includes a substrate 310, wherein first to a red pixel region RP, a green pixel region GP and a blue pixel region BP are defined, a TFT Tr over the substrate 310 and an OLED D over the TFT Tr. The OLED D is connected to the TFT Tr.

The substrate 310 can be a glass substrate or a flexible substrate.

A buffer layer 312 is formed on the substrate 310, and the TFT Tr is formed on the buffer layer 312. The buffer layer 312 can be omitted.

The TFT Tr is positioned on the buffer layer 312. The TFT Tr includes a semiconductor layer, a gate electrode, a source electrode and a drain electrode and acts as a driving element. Namely, the TFT Tr can be the driving TFT Td (of FIG. 1).

A planarization layer (or passivation layer) 350 is formed on the TFT Tr. The planarization layer 350 has a flat top surface and includes a drain contact hole 352 exposing the drain electrode of the TFT Tr.

The OLED D is disposed on the planarization layer 350 and includes a first electrode 210, an organic light emitting layer 220 and a second electrode 230. The first electrode 210 is connected to the drain electrode of the TFT Tr, and the organic light emitting layer 220 and the second electrode 230 are sequentially stacked on the first electrode 210. The OLED D is disposed in each of the red, green and blue pixel regions RP, GP and BP and emits different color light in the red, green and blue pixel regions RP, GP and BP. For example, the OLED D in the red pixel region RP can emit the red light, the OLED D in the green pixel region GP can emit the green light, and the OLED D in the blue pixel region BP can emit the blue light.

The first electrode 210 is formed to be separated in the red, green and blue pixel regions RP, GP and BP, and the second electrode 230 is formed as one-body to cover the red, green and blue pixel regions RP, GP and BP.

The first electrode 210 is one of an anode and a cathode, and the second electrode 230 is the other one of the anode and the cathode. In addition, the first electrode 210 is a reflective electrode, and the second electrode 230 is a transparent electrode (or a semi-transparent electrode). Namely, the light from the OLED D passes through the second electrode 230 to display an image. (i.e., a top-emission type organic light emitting display device)

For example, the first electrode 210 can be an anode and can include a transparent conductive oxide material layer, which can be formed of a conductive material, e.g., a transparent conductive oxide (TCO), having a relatively high work function, and a reflection layer.

The second electrode 230 can a cathode and can be formed of a conductive material having a relatively low work function. The second electrode 230 can have a thin profile to be transparent (or semi-transparent).

On the other hand, in a bottom-emission type organic light emitting display device 300, the first electrode 210 serves as a transparent electrode, and the second electrode 230 serves as a reflective electrode.

The organic light emitting layer 220 includes a first emitting part including a first EML and a first ETL, a second emitting part including a second EML and a CGL including an n-type CGL and a p-type CGL and positioned between the first and second emitting parts.

A LUMO energy level of a first compound in the first ETL is higher than that of a host, e.g., a second compound, in the n-type CGL, and a difference between the LUMO energy level of the first compound in the first ETL and the LUMO energy level of the host in the n-type CGL can be 0.3 to 1.0 eV.

In addition, a LUMO energy level of a host, e.g., a third compound, in the p-type CGL is higher than that of the host in the n-type CGL, and a difference between the LUMO energy level of the host in the p-type CGL and the LUMO energy level of the host in the n-type CGL can be 1.0 to 2.0 eV.

Moreover, a LUMO energy level of a p-type dopant in the p-type CGL is higher than a HOMO energy level of the host in the p-type CGL, and a difference between the LUMO energy level of the p-type dopant in the p-type CGL and the HOMO energy level of the host in the p-type CGL can be 0.1 to 0.5 eV.

The first compound in the first ETL and the host in the n-type CGL have the same core and different substituents.

The first emitting part can further include an HBL being adjacent to and/or contacting the first ETL. In this instance, the HBL includes a fourth compound, and the fourth compound has the same core as the first compound of the first ETL.

In the red pixel region RP, each of the first and second EMLs includes a host and a red dopant, i.e., emitter. In the green pixel region GP, each of the first and second EMLs includes a host and a green dopant. In the blue pixel region BP, each of the first and second EMLs includes a host and a blue dopant.

The OLED D can further include the capping layer on the second electrode 230. The emitting efficiency of the OLED D and/or the organic light emitting display device 300 can be further improved by the capping layer.

An encapsulation film (or an encapsulation layer) 370 is formed on the second electrode 230 to prevent penetration of moisture into the OLED D. The encapsulation film 370 can have a structure including an inorganic insulating layer and an organic insulating layer.

The organic light emitting display device 300 can include a color filter corresponding to the red, green and blue pixel regions RP, GP and BP. For example, the color filter can be positioned on or over the OLED D or the encapsulation film 370.

In addition, the organic light emitting display device 300 can further include a cover window on or over the encapsulation film 370 or the color filter. In this instance, the substrate 310 and the cover window have a flexible property such that a flexible organic light emitting display device can be provided.

Figure 4:
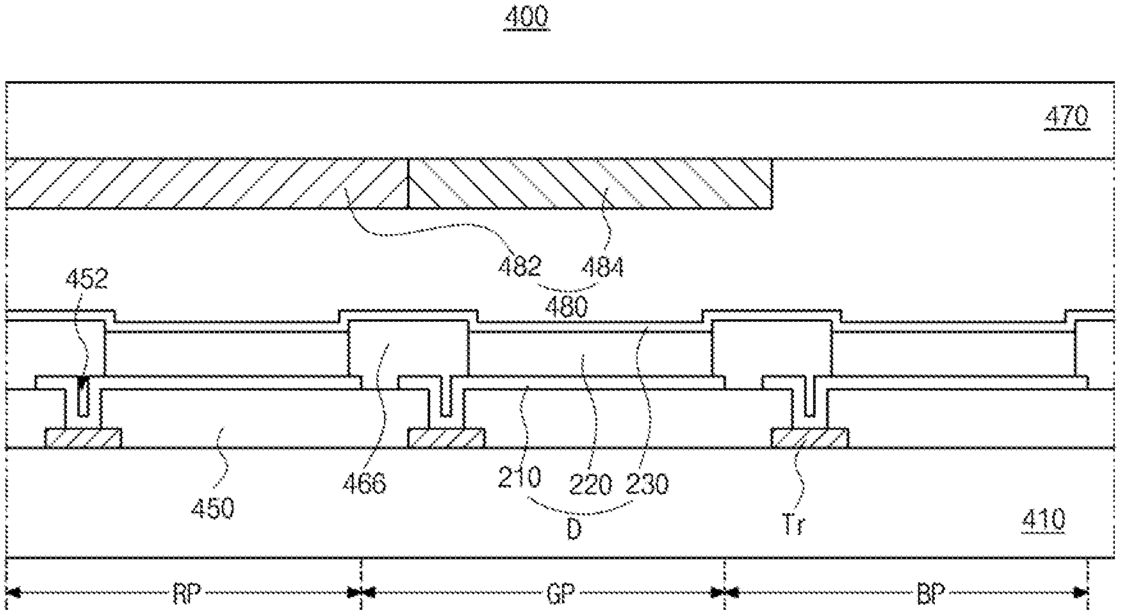
FIG. 4 is a schematic cross-sectional view of an organic light emitting display device according to a third embodiment of the present disclosure.

FIG. 4 is a schematic cross-sectional view of an organic light emitting display device according to a third embodiment of the present disclosure.

As shown in FIG. 4, the organic light emitting display device 400 includes a first substrate 410, where a red pixel RP, a green pixel GP and a blue pixel BP are defined, a second substrate 470 facing the first substrate 410, an OLED D, which is positioned between the first and second substrates 410 and 470 and providing blue emission, and a color conversion layer 480 between the OLED D and the second substrate 470.

Each of the first and second substrates 410 and 470 can be a glass substrate or a flexible substrate. For example, the flexible substrate can be one of a polyimide (PI) substrate, polyethersulfone (PES), polyethylenenaphthalate (PEN), polyethylene terephthalate (PET) and polycarbonate (PC).

A TFT Tr, which corresponding to each of the red, green and blue pixels RP, GP and BP, is formed on the first substrate 410, and a planarization layer (a passivation layer) 450, which has a drain contact hole 452 exposing an electrode, e.g., a drain electrode, of the TFT Tr is formed to cover the TFT Tr.

The OLED D including a first electrode 210, an organic light emitting layer 220 and a second electrode 230 is formed on the planarization layer 450. In this instance, the first electrode 210 can be connected to the drain electrode of the TFT Tr through the drain contact hole 452.

A bank layer 466 is formed on the planarization layer 450 to cover an edge of the first electrode 210.

The OLED D is formed in each of the red, green and blue pixels RP, GP and BP and provides the blue light. Namely, the OLED D1 is a blue OLED.

The first electrode 210 can be an anode, and the second electrode 230 can be a cathode. The first electrode 210 is a reflective electrode, and the second electrode 230 is a transparent electrode. For example, the first electrode 210 can have a structure of ITO/Ag/ITO, and the second electrode 230 can include MgAg.

The organic light emitting layer 220 includes a first emitting part including a first EML and a first ETL, a second emitting part including a second EML and a CGL including an n-type CGL and a p-type CGL and positioned between the first and second emitting parts.

A LUMO energy level of a first compound in the first ETL is higher than that of a host, e.g., a second compound, in the n-type CGL, and a difference between the LUMO energy level of the first compound in the first ETL and the LUMO energy level of the host in the n-type CGL can be 0.3 to 1.0 eV.

In addition, a LUMO energy level of a host, e.g., a third compound, in the p-type CGL is higher than that of the host in the n-type CGL, and a difference between the LUMO energy level of the host in the p-type CGL and the LUMO energy level of the host in the n-type CGL can be 1.0 to 2.0 eV.

Moreover, a LUMO energy level of a p-type dopant in the p-type CGL is higher than a HOMO energy level of the host in the p-type CGL, and a difference between the LUMO energy level of the p-type dopant in the p-type CGL and the HOMO energy level of the host in the p-type CGL can be 0.1 to 0.5 eV.

The first compound in the first ETL and the host in the n-type CGL have the same core and different substituents.

The first emitting part can further include an HBL being adjacent to and/or contacting the first ETL. In this instance, the HBL includes a fourth compound, and the fourth compound has the same core as the first compound of the first ETL.

Each of the first and second EMLs includes a host and a blue dopant.

The color conversion layer 480 includes a first color conversion layer 482 corresponding to the red pixel RP and a second color conversion layer 484 corresponding to the green pixel GP. For example, the color conversion layer 480 can include an inorganic color conversion material such as a quantum dot. The color conversion layer 480 is not presented in the blue pixel BP so that the OLED D in the blue pixel can directly face the second electrode 470.

The blue light from the OLED D in the red pixel region RP is converted into the red light by the first color conversion layer 482 in the red pixel RP, and the blue light from the OLED D in the green pixel region GP is converted into the green light by the second color conversion layer 484 in the green pixel GP.

A color filter can be formed between the second substrate 470 and the color conversion layer 480. For example, a red color filter can be formed between the first color conversion layer 482 and the second substrate 470, and a green color filter can be formed between the second color conversion layer 484 and the second substrate 470.

Accordingly, the organic light emitting display device 400 can display a full-color image.

On the other hand, when the light from the OLED D passes through the first substrate 410, i.e., a bottom-emission type OLED, the color conversion layer 480 is disposed between the OLED D and the first substrate 410.

In the organic light emitting display device 400, the OLED D emitting the blue light is formed in all of the red, green and blue pixel regions RP, GP and BP, and a full color image is provided by using the color conversion layer 480.

Figure 5:
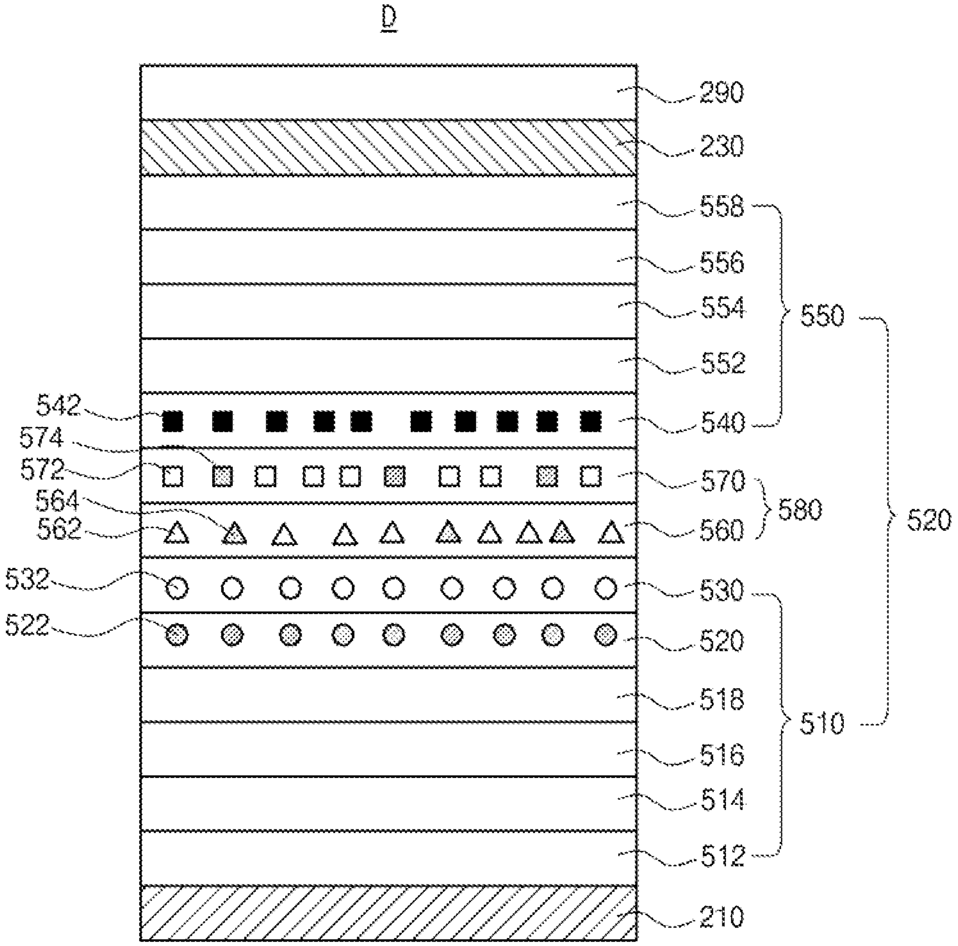
FIG. 5 is a schematic cross-sectional view of a blue OLED according to a fourth embodiment of the present disclosure.

FIG. 5 is a schematic cross-sectional view of a blue OLED according to a fourth embodiment of the present disclosure.

As shown in FIG. 5, the OLED D includes a first electrode 210, a second electrode 230 facing the first electrode 210 and an organic light emitting layer 520 between the first and second electrodes 210 and 230. The organic light emitting layer 520 includes a first emitting part 510 including a first EML 518 and a first ETL 530, a second emitting part 550 including a second EML 554 and positioned between the first emitting part 510 and the second electrode 230 and a CGL 580 including an n-type CGL 560 and a p-type CGL 570 and positioned between the first and second emitting parts 510 and 550.

The first electrode 210 can be a reflective electrode, and the second electrode 230 can be a transparent electrode. In this instance, the OLED D can further include a capping layer 290 on or over the second electrode 230.

Alternatively, the first electrode 210 can be a transparent electrode, and the second electrode 230 can be a reflective electrode.

The first emitting part 510 can further include an HBL 520 between the first EML 518 and the first ETL 530.

In addition, the first emitting part 510 can further include at least one of a first EBL 516 under the first EML 518, a first hole transporting layer (HTL) 514 under the first EBL 516 and a hole injection layer (HIL) 512 under the first HTL 514.

The second emitting part 550 can further include a second HTL 540 under the second EML 554.

In addition, the second emitting part 550 can further include at least one of a second EBL 552 between second EML 554 and the second HTL 540, a second ETL 556 on the second EML 554 and an electron injection layer (EIL) 558 on the second ETL 556.

In the first emitting part 510, one surface, e.g., a lower surface, of the first EML 518 contacts the EBL 516, and the other surface, e.g., an upper surface, of the first EML 518 contacts the HBL 520. On the other hand, a HBL is not presented in the second emitting part 550. As a result, in the second emitting part 550, one surface, e.g., a lower surface, of the second EML 554 contacts the EBL 552, and the other surface, e.g., an upper surface, of the EML 554 contact the ETL 556.

The CGL 580 is positioned between the first and second emitting parts 510 and 550, and the first and second emitting parts 510 and 550 are connected to each other by the CGL 580. Namely, the first emitting part 510 is positioned between the first electrode 210 and the CGL 580, and the second emitting part 550 is positioned between the second electrode 230 and the CGL 580.

The n-type CGL 560 of the CGL 580 is positioned between the first ETL 530 and the second HTL 540, and the p-type CGL 570 of the CGL 580 is positioned between the n-type CGL 560 and the second HTL 540. The n-type CGL 560 provides an electron to the first EML 518 of the first emitting part 510, and the p-type CGL 570 provides a hole to the second EML 554 of the second emitting part 550.

The first ETL 530 includes a first compound, e.g., an electron transporting material, 532 represented by Formula 1.

[Formula 1]

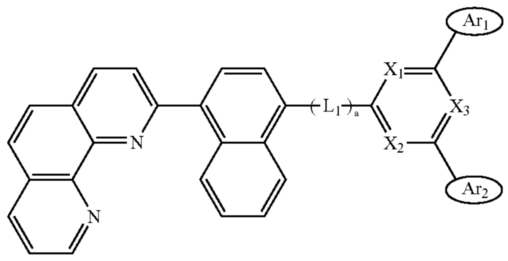

In Formula 1, each of $X_1$, $X_2$ and $X_3$ is independently N or CR, and at least one of $X_1$, $X_2$ and $X_3$ is N. R is selected from the group consisting of hydrogen, a substituted or unsubstituted C1 to C10 alkyl group, a substituted or unsubstituted C6 to C30 aryl group and a substituted or unsubstituted C3 to C30 heteroaryl group.

$L_1$ is a substituted or unsubstituted C6 to C30 arylene group, and a is 0 or 1.

Each of $Ar_1$ and $Ar_2$ is independently selected from the group consisting of a substituted or unsubstituted C6 to C30 aryl group and a substituted or unsubstituted C3 to C30 heteroaryl group.

In the present disclosure, without specific definition, a substituent of an alkyl group, an aryl group, a heteroaryl group, an arylene group, a heteroarylene group and an arylamine group can be at least one of deuterium, halogen, cyano, a C1 to C10 alkyl group and a C6 to C30 aryl group.

In the present disclosure, the C6 to C30 aryl group (or C6 to C30 arylene group) can be selected from the group consisting of phenyl, biphenyl, terphenyl, naphthyl, anthracenyl, pentalenyl, indenyl, indenoindenyl, heptalenyl, biphenylenyl, indacenyl, phenanthrenyl, benzophenanthrenyl, dibenzophenanthrenyl, azulenyl, pyrenyl, fluoranthenyl, triphenylenyl, chrysenyl, tetraphenyl, tetrasenyl, picenyl, pentaphenyl, pentacenyl, fluorenyl, indenofluorenyl and spiro-fluorenyl.

In the present disclosure, the C5 to C30 heteroaryl group can be selected from the group consisting of pyrrolyl, pyridinyl, pyrimidinyl, pyrazinyl, pyridazinyl, triazinyl, tetrazinyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, quinolinyl, isoquinolinyl, phthalazinyl, quinoxalinyl, cinnolinyl, quinazolinyl, quinozolinyl, quinolinyl, purinyl, phthalazinyl, quinoxalinyl, benzoquinolinyl, benzoisoquinolinyl, benzoquinazolinyl, benzoquinoxalinyl, acridinyl, phenanthrolinyl, perimidinyl, phenanthridinyl, pteridinyl, cinnolinyl, naphtharidinyl, furanyl, oxazinyl, oxazolyl, oxadiazolyl, triazolyl, dioxynyl, benzofuranyl, dibenzofuranyl, thiopyranyl, xanthenyl, chromanyl, isochromanyl, thioazinyl, thiophenyl, benzothiophenyl, dibenzothiophenyl, difuropyrazinyl, benzofurodibenzofuranyl, benzothienobenzothiophenyl, benzothienodibenzothiophenyl, benzothienobenzofuranyl, and benzothienodibenzofuranyl.

For example, in Formula 1, two or three of $X_1$, $X_2$ and $X_3$ can be N, and L1 can be phenylene. Each of $Ar_1$ and $Ar_2$ can be independently selected from the group consisting of phenyl, biphenyl, naphthyl, phenanthrenyl, phenylcarbazolyl, spiro-fluorenyl and dibenzofuranyl.

Namely, the first compound 532 included in the first ETL 530 has a structure in which a hetero ring containing at least one nitrogen atom is connected (linked, combined or joined) to a phenanthroline moiety through at least one linker. As a result, the first compound 532 has a relatively high LUMO energy level. For example, the LUMO energy level of the first compound 532 can be about 2.5 to 3.0 eV. In addition, the first compound 532 has a relatively high HOMO energy level. For example, the HOMO energy level of the first compound 532 can be about 5.5 to 5.8 eV.

For example, the first compound 532 can be one of the compounds in Formula 2.

[Formula 2]

A-01

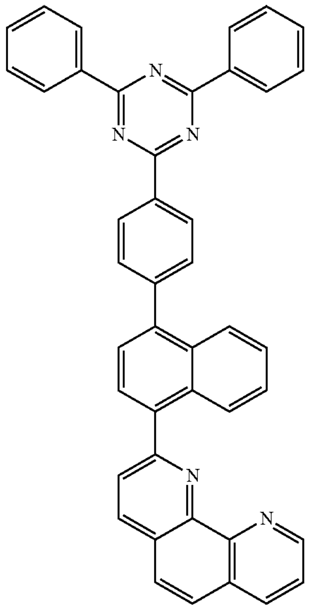

A-02

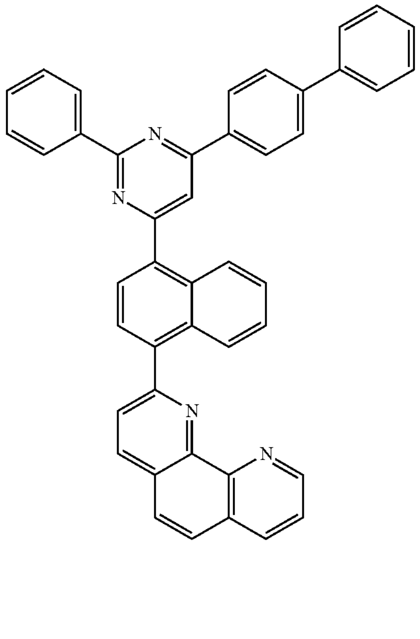

-continued
A-03
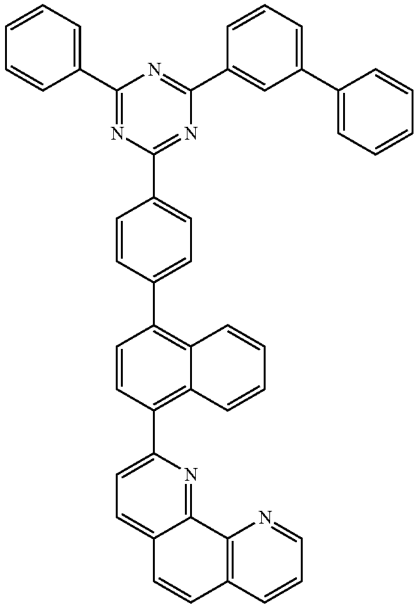
A-04
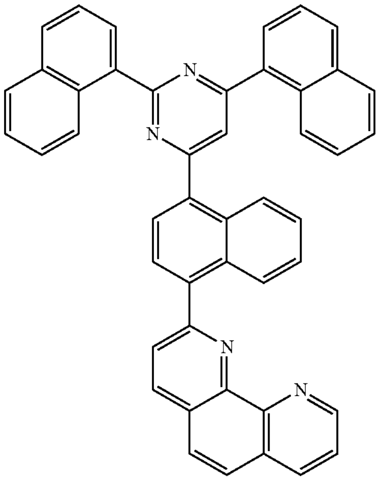
-continued
A-05
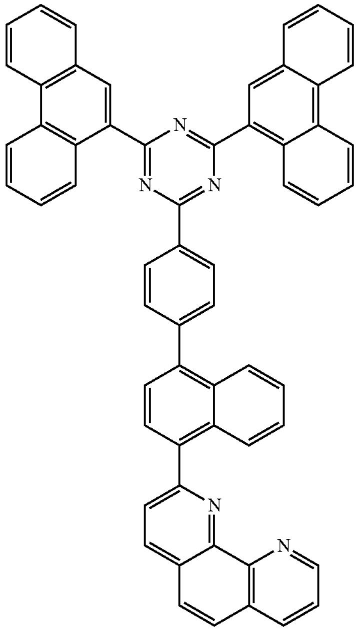
A-06
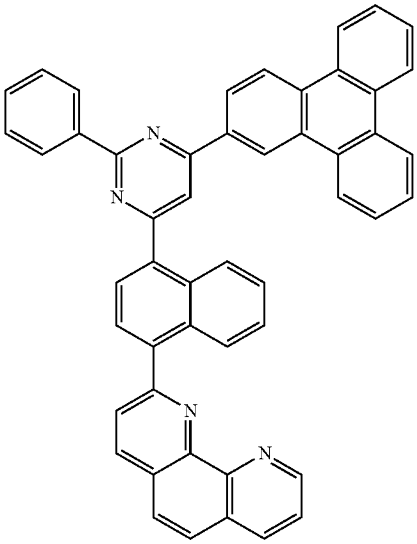

-continued

A-07

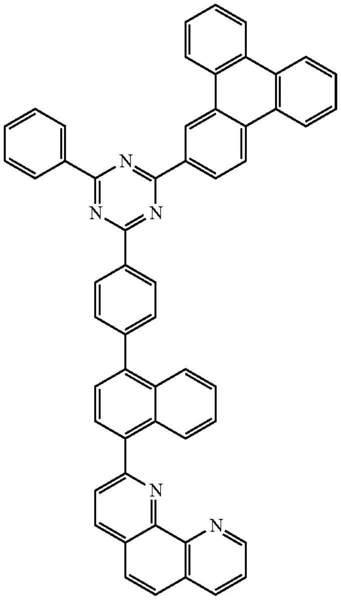

A-08

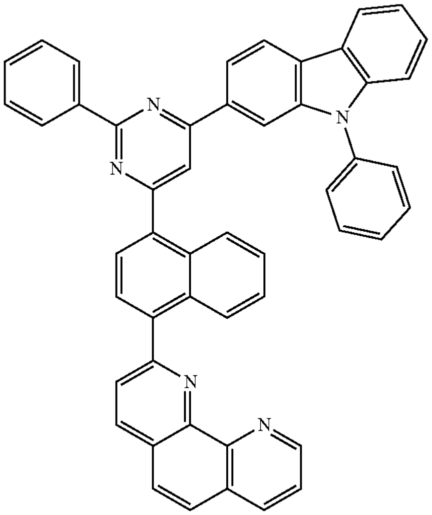

-continued

A-09

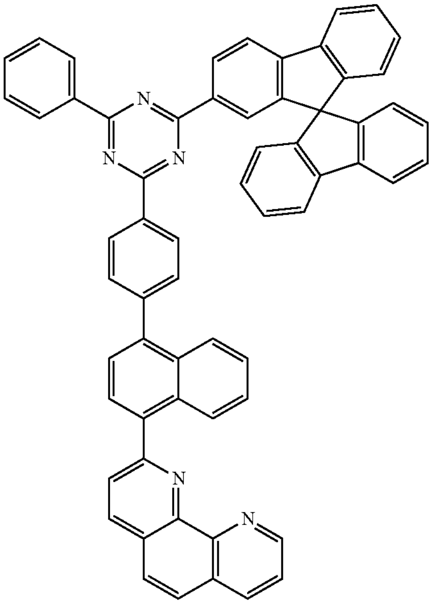

A-10

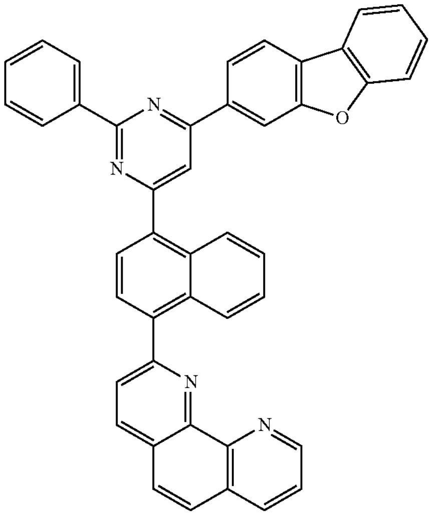

The first ETL 530 can have a thickness of about 90 to 110 Å and can consist of the first compound 532. Namely, the first compound 532 can have a weight % of 100 in the first ETL 530.

The HBL 520, which is disposed under the first ETL 530 and contacts the first ETL 530, includes a hole blocking material 522. The hole blocking material 522 can be represented by Formula 1 and can be same as or different from the first compound 532. The HBL 520 can have a thickness being smaller than the first ETL 530. For example, the HBL 520 can have a thickness of about 70 to 90 Å.

Since the first compound 532 in the first ETL 530 and the hole blocking material 522 in the HBL 520 have the same core, an interfacial property between the first ETL 530 and the HBL 520 is improved.

In the CGL 580, the n-type CGL 560 includes a second compound 562, e.g., a host, and an n-type dopant 564. In the n-type CGL 560, a weight % of the second compound 562 is greater than that of the n-type dopant 564. For example, the n-type dopant 564 can be Li or Cs and can have a weight % of about 0.5 to 5 in the n-type CGL 560.

The n-type CGL 560 can have a thickness being greater than the first ETL 530. For example, the n-type CGL 560 can have a thickness of about 180 to 220 Å.

The second compound 562 is represented by Formula 3.

[Formula 3]

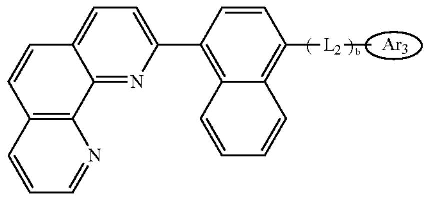

In Formula 3, $L_2$ is a substituted or unsubstituted C6 to C30 arylene group, and b is 0 or 1. $Ar_3$ is selected from the group consisting of a substituted or unsubstituted C6 to C30 aryl group and a substituted or unsubstituted C3 to C30 heteroaryl group containing at least one of O and S.

For example, $L_2$ can be phenylene or naphthylene. $Ar_3$ can be selected from the group consisting of phenanthrenyl, pyrenyl, dibenzofuranyl, benzonaphthothiophenyl), isochrysenyl, naphthylanthracenyl, spiro-fluorenyl, spiro[fluorene-9,9'-xanthene] and benzonaphthofuranyl.

Namely, the second compound 562 included in the n-type CGL 560 has a structure in which an aromatic ring, e.g., an aryl group, or a hetero ring, e.g., a heteroaryl group, containing at least one of O or S is connected to a phenanthroline moiety through at least one linker. As a result, the second compound 562 has a relatively low LUMO energy level. For example, the LUMO energy level of the second compound 562 can be about 3.0 to 3.5 eV. In addition, the second compound 562 has a relatively low HOMO energy level. For example, the HOMO energy level of the second compound 562 can be about 5.8 to 6.2 eV.

For example, the second compound 562 can be one of the compounds in Formula 4.

[Formula 4]

B-01

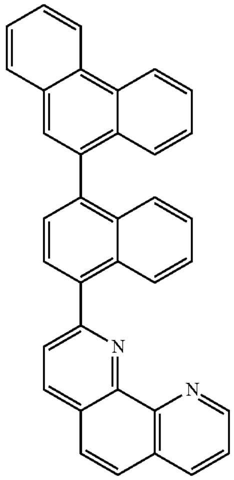

-continued

B-02

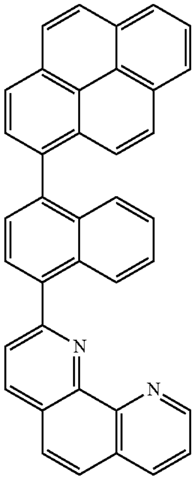

B-03

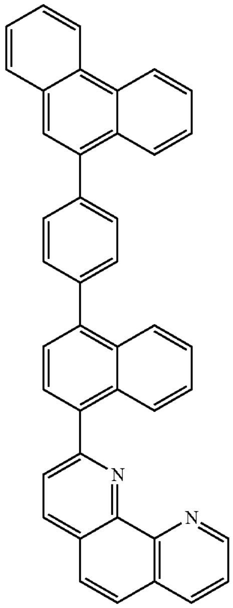

B-04
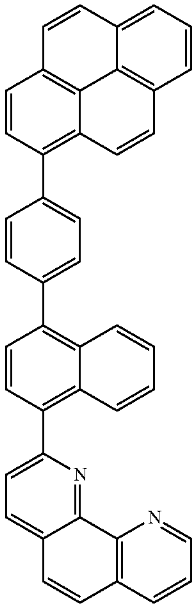
B-05
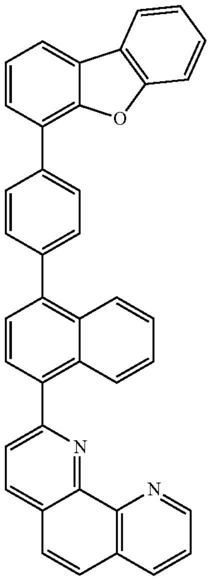
B-06
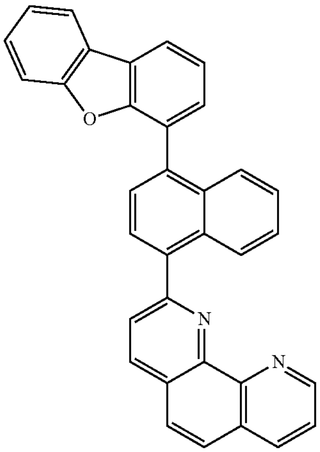
B-07
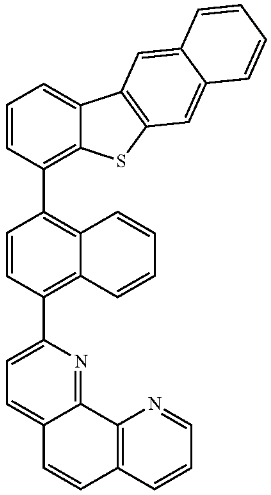
B-08
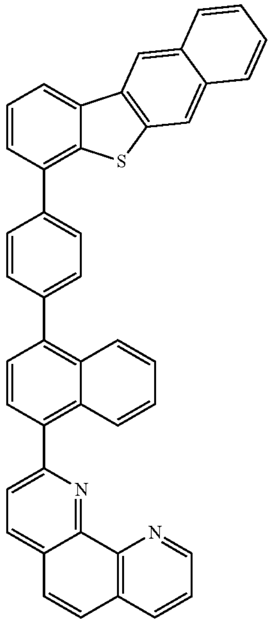

B-09
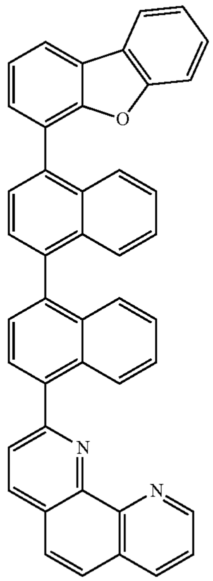
B-10
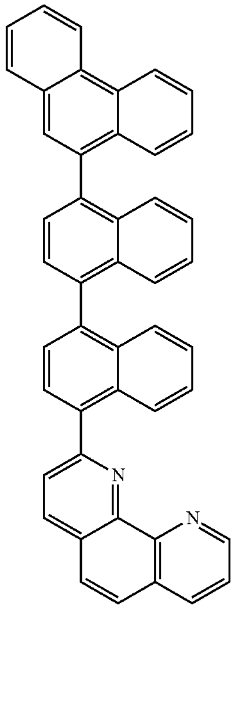
B-11
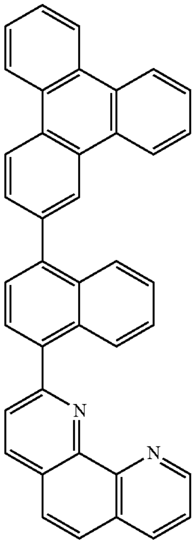
B-12
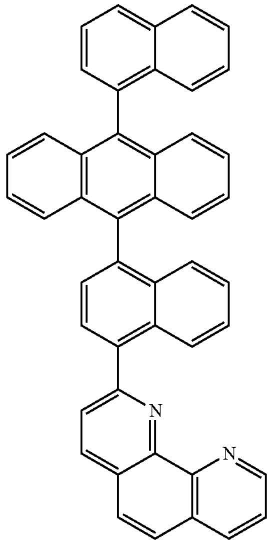

-continued
B-13
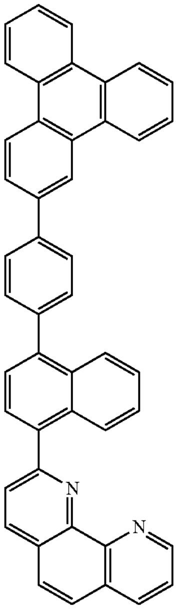
B-14
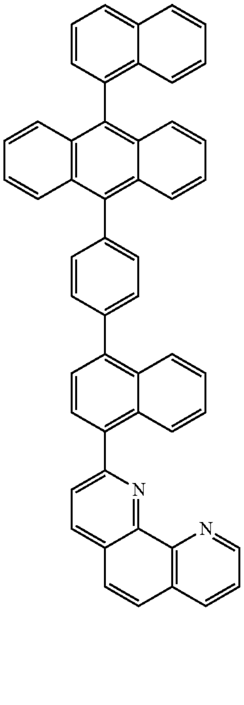
-continued
B-15
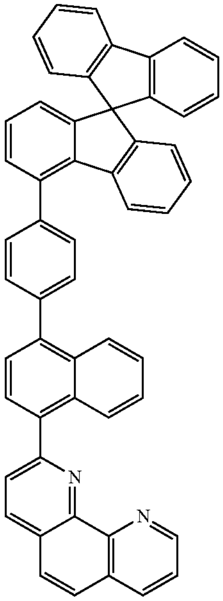
B-16
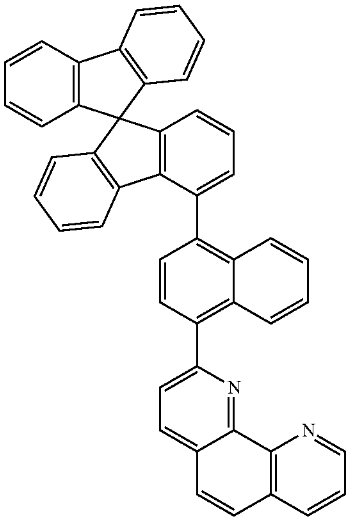

-continued

B-17

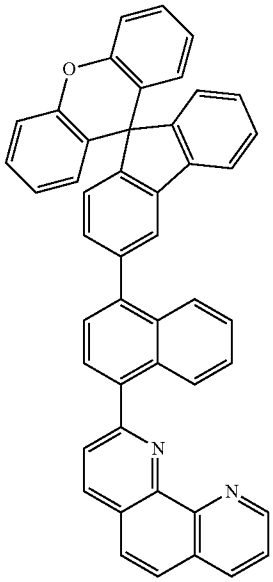

B-18

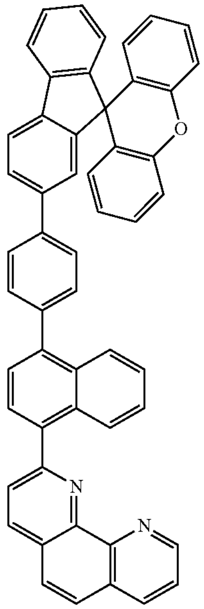

-continued

B-19

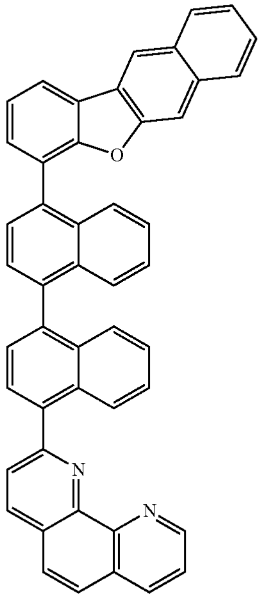

B-20

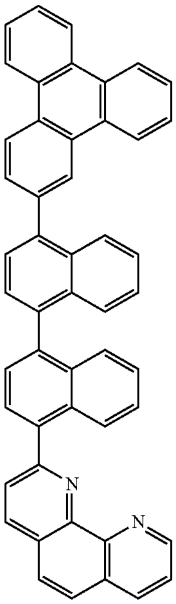

As shown in Formula 1 and Formula 3, the first compound 532 in the first ETL 530 and the second compound 562 in the n-type CGL 560 have the same core, i.e., the phenanthroline moiety, and have different sub stituent. Namely, the first compound 532 in the first ETL 530 has a structure in which a hetero ring containing at least one nitrogen atom is connected (linked, combined or joined) to a phenanthroline moiety through at least one linker, while the second compound 562 in the n-type CGL 560 has a structure in which a ring not containing a nitrogen atom, i.e., an aryl group or a heteroaryl group containing at least one of O or S, is connected to a phenanthroline moiety through at least one linker. As a result, an interfacial property between the first ETL 530 and the n-type CGL 560, which contacts each other, is improved.

A LUMO energy level of the first compound 532 in the first ETL 530 is higher than that of the second compound 562 in the n-type CGL 560. A difference between the LUMO energy level of the first compound 532 in the first ETL 530 and the LUMO energy level of the second compound 562 in the n-type CGL 560 can be 0.3 to 1.0 eV. For example, the difference between the LUMO energy level of the first compound 532 in the first ETL 530 and the LUMO energy level of the second compound 562 in the n-type CGL 560 can be 0.3 to 0.7 eV.

In the CGL 580, the p-type CGL 570 includes a third compound 572, e.g., a host, and a p-type dopant 574. In the p-type CGL 570, a weight % of the third compound 572 is greater than that of the p-type dopant 574.

The third compound 572 is represented by Formula 5.

[Formula 5]

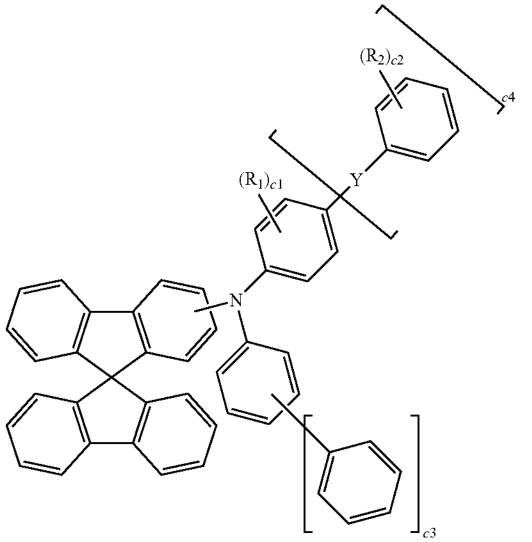

In Formula 5, each of $R_1$ and $R_2$ is independently selected from the group consisting of a substituted or unsubstituted C1 to C10 alkyl group and a substituted or unsubstituted C6 to C30 aryl group, or $R_1$ and $R_2$ are connected to form a ring. Y is a single bond (direct bond) or $NR_3$, and $R_3$ is selected from the group consisting of hydrogen, a substituted or unsubstituted C1 to C10 alkyl group and a substituted or unsubstituted C6 to C30 aryl group. In addition, $C_1$ is an integer of 0 to 4, $C_2$ is an integer of 0 to 5, and each of $C_3$ and $C_4$ is independently 0 or 1.

Namely, the third compound 572 included in the p-type CGL 570 has a structure in which an amino group connected to a spiro-fluorene moiety. As a result, the third compound 572 has a relatively high LUMO energy level. For example, the LUMO energy level of the third compound 572 can be about 1.1 to 1.8 eV. In addition, the third compound 572 has a relatively high HOMO energy level. For example, the HOMO energy level of the third compound 572 can be about 5.0 to 5.7 eV.

For example, the third compound 572 can be one of the compounds in Formula 6.

[Formula 6]

C-01

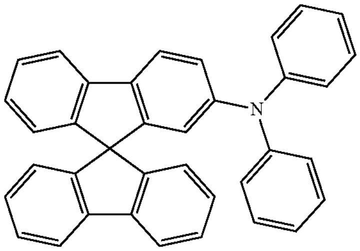

C-02

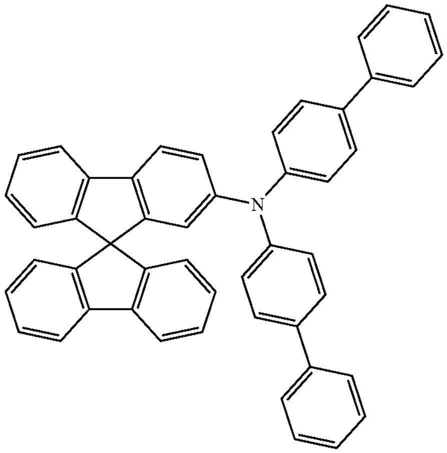

C-03

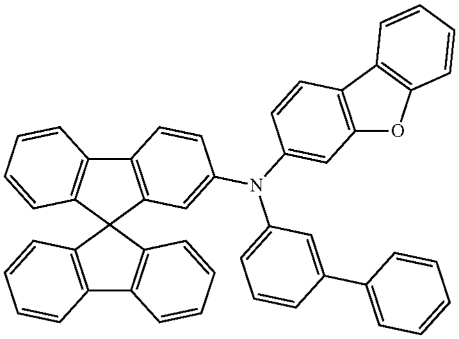

C-04

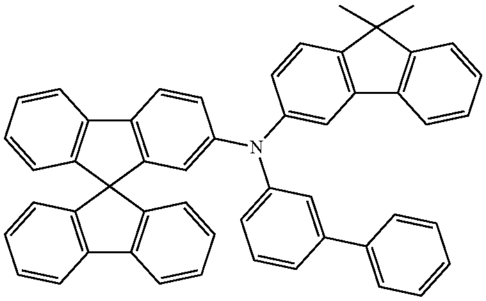

-continued
C-05
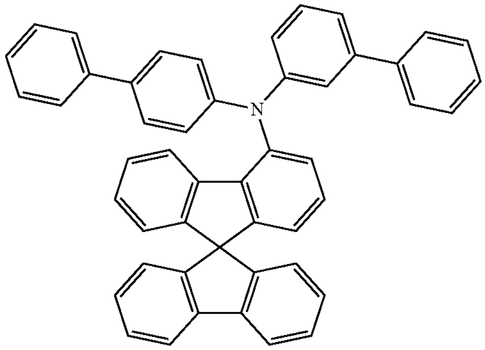
C-06
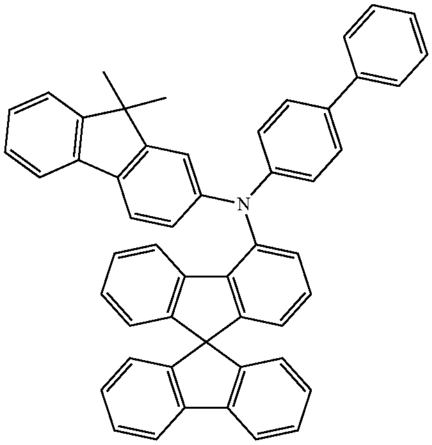
C-07
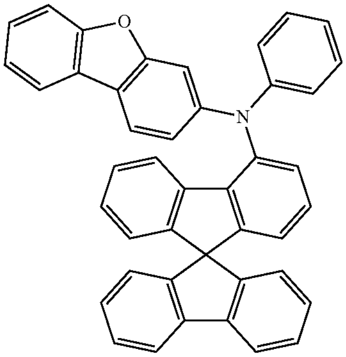
C-08
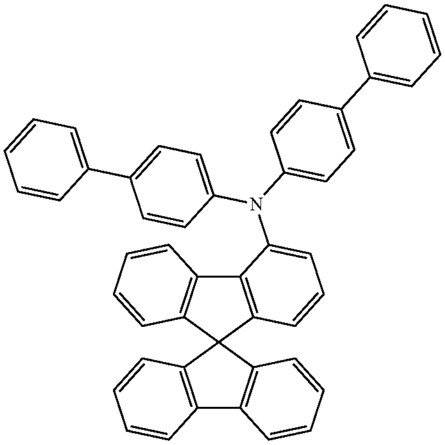
-continued
C-09
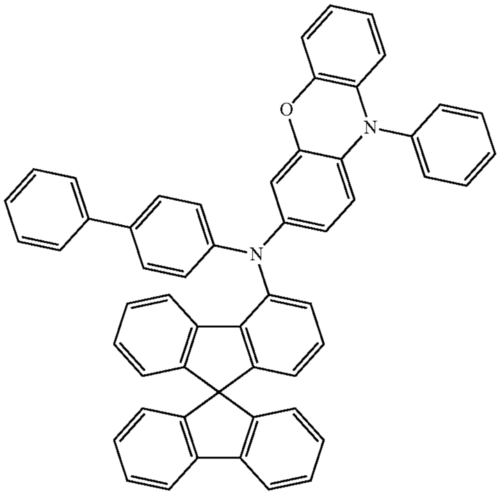
C-10
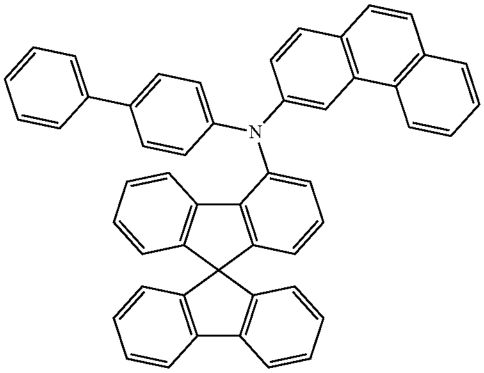
The p-type dopant 574 can have a LUMO energy level of about 5.0 to 5.1 eV and can have a weight % of about 3 to 15 wt % in the p-type CGL 570.
The p-type dopant 574 can be the compound in Formula 7.
[Formula 7]
PD-01
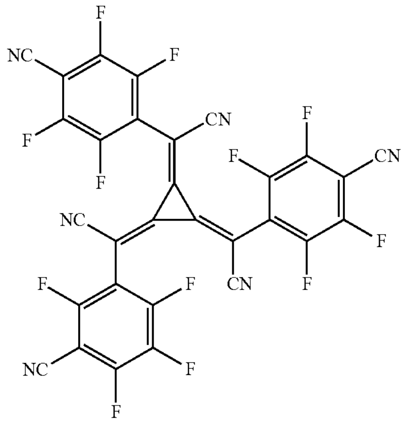

The p-type CGL 570 can have a thickness being smaller than the n-type CGL 560. For example, the p-type CGL 570 can have a thickness of about 80 to 120 Å.

In the CGL 580, a LUMO energy level of the third compound 572 in the p-type CGL 570 is higher than that of the second compound 562 in the n-type CGL 560. In addition, a difference between the LUMO energy level of the third compound 572 in the p-type CGL 570 and the LUMO energy level of the second compound 562 in the n-type CGL 560 can be 1.0 to 2.0 eV. For example, the difference between the LUMO energy level of the third compound 572 in the p-type CGL 570 and the LUMO energy level of the second compound 562 in the n-type CGL 560 can be 1.5 to 2.0 eV.

Moreover, a LUMO energy level of the p-type dopant 574 in the p-type CGL 570 is higher than a HOMO energy level of the third compound 572 in the p-type CGL 570, and a difference between the LUMO energy level of the p-type dopant 574 in the p-type CGL 570 and the HOMO energy level of the third compound 572 in the p-type CGL 570 can be 0.1 to 0.5 eV.

The second HTL 540, which is disposed on the p-type CGL 570 and contacts the p-type CGL 570, includes a hole transporting material 542. The hole transporting material 542 can be represented by Formula 5 and can be same as or different from the third compound 572. A difference between a LUMO energy level of the hole transporting material 542 and the LUMO energy level of the third compound 572 in the p-type CGL 570 can be 0 to 0.2 eV.

The second HTL 540 has a thickness being greater than the p-type CGL 570. For example, the second HTL 540 can have a thickness of about 450 to 550 Å.

Since the hole transporting material 542 in the second HTL 540 and the third compound 572 in the p-type CGL 570 have the same core, an interfacial property between the second HTL 540 and the p-type CGL 570 is improved.

Figure 6:
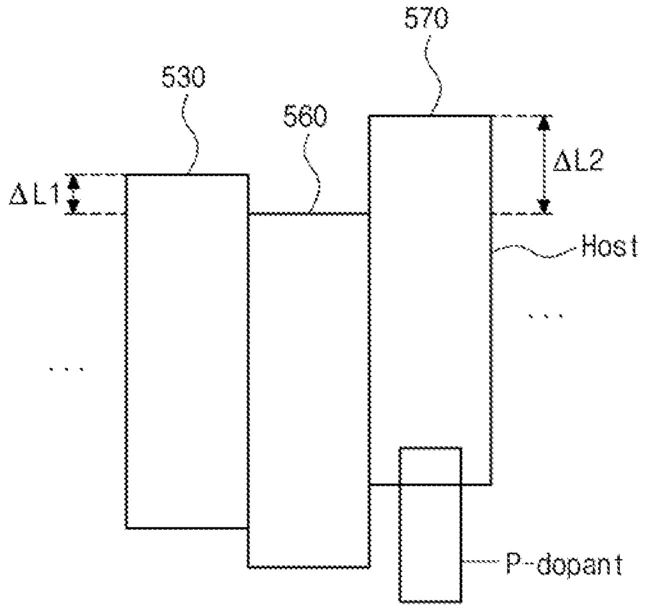
FIG. 6 is an energy band diagram of a part of an OLED of the present disclosure.

Referring to FIG. 6, which is an energy band diagram of a part of an OLED of the present disclosure, the first ETL 530, the n-type CGL 560, the p-type CGL 570 and the second HTL 540 are sequentially disposed (stacked). In this instance, the LUMO energy level of the first compound 532 in the first ETL 530 is higher than that of the second compound 562, e.g., the host, in the n-type CGL 560 and lower than that of the third compound 572, e.g., the host, in the p-type CGL 570. In addition, the HOMO energy level of the first compound 532 in the first ETL 530 is higher than that of the second compound 562 in the n-type CGL 560 and lower than that of the third compound 572 in the p-type CGL 570. Moreover, in the p-type CGL 570, the LUMO energy level of the p-type dopant 574 is higher than the HOMO energy level of the third compound 572, and a difference between the LUMO energy level of the p-type dopant 574 and the HOMO energy level of the third compound 572 can be 0.1 to 0.5 eV.

As a result, the driving voltage of the tandem structure OLED D is reduced.

Furthermore, a difference "ΔL1" between the LUMO energy level of the first compound 532 in the first ETL 530 and the LUMO energy level of the second compound 562 in the n-type CGL 560 is smaller than a difference "ΔL2" between the LUMO energy level of the second compound 562 in the n-type CGL 560 and the LUMO energy level of the third compound 572 in the p-type CGL. As a result, the driving voltage of the tandem structure OLED D is further reduced.

Since the first compound 532 in the first ETL 530 and the second compound 562 in the n-type CGL 560 have the same core, an interfacial property between the first ETL 530 and the n-type CGL 560 is improved so that the driving voltage of the tandem structure OLED D is further reduced.

Since the hole blocking material 522 in the HBL 520 and the first compound 532 in the first ETL 530 have the same core, an interfacial property between the first ETL 530 and the HBL 520 is improved so that the driving voltage of the tandem structure OLED D is further reduced.

Since the hole transporting material 542 in the HTL 540 and the third compound 572 in the p-type CGL 570 have the same core, an interfacial property between the HTL 540 and the p-type CGL 570 is improved so that the driving voltage of the tandem structure OLED D is further reduced.

The first HTL 514 can have a thickness being smaller than the second HTL 540. For example, the first HTL 514 can have a thickness of about 350 to 450 Å.

The first HTL 514 can include the compound in Formula 8.

[Formula 8]

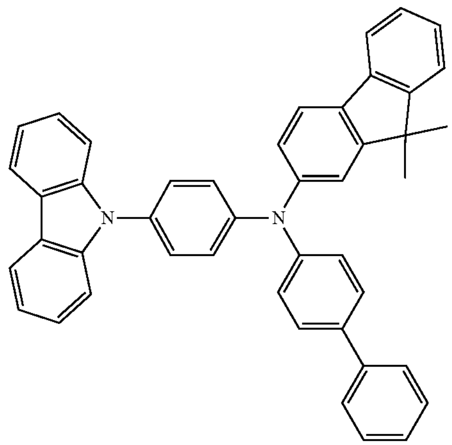

Alternatively, each of the first HTL 514 can include one of the compounds selected from the group consisting of N,N'-diphenyl-N,N'-bis(3-methylphenyl)-1,1'-biphenyl-4,4'-diamine; TPD), N,N'-diphenyl-N,N'-bis(1-naphthyl)-1,1'-biphenyl-4,4"-diamine(NPB; NPD), 4,4'-bis(N-carbazolyl)-1,1'-biphenyl(CBP), poly[N,N'-bis(4-butylphenyl)-N,N'-bis(phenyl)-benzidine](Poly-TPD), (poly[(9,9-dioctylfluorenyl-2,7-diyl)-co-(4,4'-(N-(4-sec-butylphenyl)diphenylamine))](TFB), di-[4-(N,N-di-p-tolyl-amino)-phenyl]cyclohexane(TAPC), 3,5-di(9H-carbazol-9-yl)-N,N-diphenylaniline(DCDPA), N-(biphenyl-4-yl)-9,9-dimethyl-N-(4-(9-phenyl-9H-carbazol-3-yl)phenyl)-9H-fluoren-2-amine and N-(biphenyl-4-yl)-N-(4-(9-phenyl-9H-carbazol-3-yl)phenyl)biphenyl-4-amine.

The HIL 512 can have a thickness being smaller than the first HTL 514. For example, the HIL 512 can have a thickness of about 40 to 60 Å.

The HIL 512 can includes the compound in Formula 7 and the compound in Formula 8. For example, in the HIL 512, the compound in Formula 7 can have a weight % of 1 to 10.

Alternatively, HIL 512 can include one of the compounds selected from the group consisting of 4,4',4"-tris(3-methylphenylamino)triphenylamine (MTDATA), 4,4',4"-tris(N,N-diphenyl-amino)triphenylamine(NATA), 4,4',4"-tris(N-(naphthalene-1-yl)-N-phenyl-amino)triphenylamine(1T-NATA), 4,4',4"-tris(N-(naphthalene-2-yl)-N-phenyl-amino)triphenylamine(2T-NATA), copper phthalocyanine(CuPc), tris(4-carbazoyl-9-yl-phenyl)amine(TCTA), NPB (or NPD), 1,4,5,8,9,11-hexaazatriphenylenehexacarbonitrile (dipyrazino[2,3-f:2'3'-h]quinoxaline-2,3,6,7,10,11-hexacarbonitrile; HAT-CN), 1,3,5-tris[4-(diphenylamino)phenyl] benzene(TDAPB), poly(3,4-ethylenedioxythiphene) polystyrene sulfonate(PEDOT/PSS) and N-(biphenyl-4-yl)-9,9-dimethyl-N-(4-(9-phenyl-9H-carbazol-3-yl)phenyl)-9H-fluoren-2-amine.

The second ETL 556 can have a thickness being greater than the first ETL 530. For example, the second ETL 556 can have a thickness of about 250 to 350 Å.

The second ETL 556 can include the compound in Formula 1 or the compound in Formula 13.

[Formula 13]

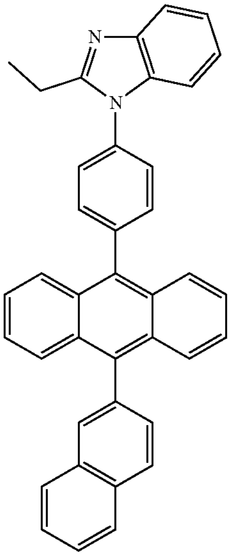

Alternatively, second ETL 556 can include one of the compounds selected from the group consisting of tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-tris(N-phenylbenzimidazol-2-yl)benzene (TPBi), bis(2-methyl-8-quinolinolato-N1,O8)-(1,1'-biphenyl-4-olato)aluminum (BAlq), 4,7-diphenyl-1,10-phenanthroline (Bphen), 2,9-bis(naphthalene yl)4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tri(p-pyrid-3-yl-phenyl)benzene (TpPyPB), 2,4,6-tris(3'-(pyridin-3-yl)biphenyl-3-yl)1,3,5-triazine (TmPPPyTz), poly[9,9-bis(3'-((N,N-dimethyl)-N-ethylammonium)-propyl)-2,7-fluorene]-alt-2,7-(9,9-dioctylfluorene)] (PFNBr), tris(phenylquinoxaline (TPQ) and diphenyl-4-triphenylsilyl-phenylphosphine oxide (TSPO1).

The EIL 558 can include at least one of an alkali halide compound, such as LiF, CsF, NaF, or $BaF_2$, and an organometallic compound, such as lithium benzoate or sodium stearate. The EIL 558 can have a thickness of 20 to 40 Å.

Each of the first and second EBLs 516 and 552 can include the compound in Formula 9.

[Formula 9]

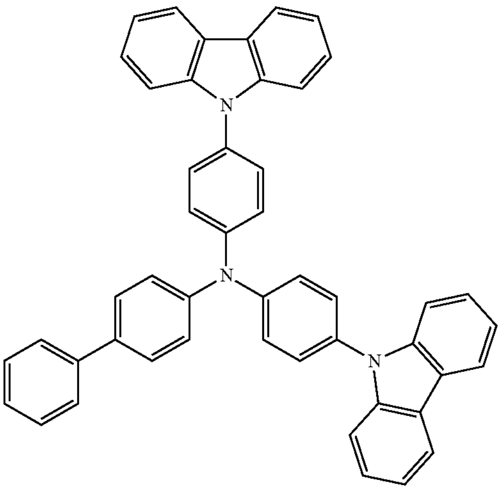

A thickness of the first EBL 516 can be smaller than that of the second EBL 552. For example, the first EBL 516 can have a thickness of about 65 to 85 Å, and the second EBL 552 can have a thickness of about 90 to 110 Å.

Alternatively, each of the first and second EBLs 516 and 552 can include one of compounds selected from the group consisting of TCTA, tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, MTDATA, 1,3-bis(carbazol-9-yl)benzene(mCP), 3,3'-bis(N-carbazolyl)-1,1'-biphenyl(mCBP), CuPc, N,N'-bis[4-[bis(3-methylphenyl)amino]phenyl]-N,N'-diphenyl]4,1'-biphenyl]-4,4'-diamine(DNTPD), TDAPB, DCDPA and 2,8-bis(9-phenyl-9H-carbazol-3-yl)dibenzo[b,d]thiophene).

The first EML 518 includes a first host and a first dopant, e.g., an emitter, and the second EML 554 includes a second host and a second dopant. The first dopant can have a weight % of about 1 to 10 in the first EML 518, and the second dopant can have a weight % of about 1 to 10 in the second EML 554. Each of the first and second EMLs 518 and 554 can have a thickness of about 150 to 250 Å.

The first EML 518 and the second EML 554 can emit the same color light. For example, a difference between an emission wavelength of the first EML 518 and an emission wavelength of the second EML 554 can be 20 nm or less.

For example, in the first and second EMLs 518 and 554, each of the first and second hosts can be an anthracene derivative (compound), and each of the first and second dopants can be a boron derivative. In an exemplary embodiment of the present disclosure, each of the first and second hosts in the first and second EMLs 518 and 554 can be the compound in Formula 10, and each of the first and second dopants in the first and second EMLs 518 and 554 can be the compound in Formula 11.

[Formula 10]

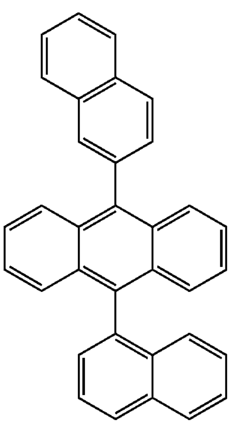

[Formula 11]

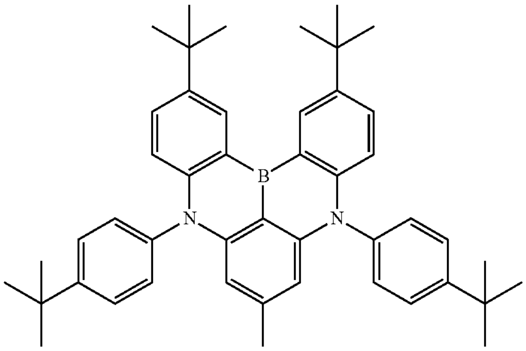

Alternatively, the first EML 518 and the second EML 554 can emit different color lights.

The capping layer 290 is positioned on or over the second electrode 230 being the transparent electrode. For example, the capping layer 290 can include the material of the first HTL 514 or the material of the second HTL 540 and can have a thickness of about 400 to 600 Å.

In FIG. 5, the OLED D has a double stack structure including the first emitting part 510 and the second emitting part 550. Alternatively, the OLED D can further include additional emitting part positioned between the first emitting part 510 and the first electrode 210 and/or between the second emitting part 550 and the second electrode 230. For example, the OLED D further includes a third emitting part between the first emitting part 510 and the first electrode 210, each of the second emitting part 550 and the third emitting part emit blue light, and the first emitting part 510 emits red and green light. As a result, a white OLED D is provided. In this case, additional CGL including an n-type CGL and a p-type CGL can be disposed between the first emitting part 510 and the third emitting part.

As illustrated above, in the OLED of the present disclosure, the first ETL 530, the n-type CGL 560 and the p-type CGL 570, which are sequentially disposed, meet the above conditions so that the driving voltage of the OLED D is reduced.

In addition, at least one of an interfacial property between the HBL 520 and the first ETL 530, an interfacial property between the first ETL 530 and the n-type CGL 560 and an interfacial property between the p-type CGL 570 and the second HTL 540 is improved so that the driving voltage of the OLED D is further reduced.

[OLED 1]

An anode (ITO/APC/ITO), an HIL (the compound in Formula 8 and the compound in Formula 7 (5 wt % doping), 50 Å), a first HTL (the compound in Formula 8, 400 Å), a first EBL (the compound in Formula 9, 75 Å), a first EML (the compound in Formula 10 and the compound in Formula 11 (3 wt % doping), 200 Å), an HBL (80 Å), a first ETL (100 Å), an n-type CGL (200 Å), a p-type CGL (100 Å), a second HTL (500 Å), a second EBL (the compound in Formula 9, 100 Å), a second EML (the compound in Formula 10 and the compound in Formula 11 (3 wt % doping), 200 Å), a second ETL (the compound in Formula 13, 300 Å), an EIL (LiF, 30 Å), a cathode (Al, 200 Å) and a capping layer (the compound in Formula 8, 500 Å) are sequentially stacked to form the OLED.

1. Comparative Example (1) Comparative Example 1 (Ref1)

The compound E-01 in Formula 12 is used to form the HBL, the compound F-01 in Formula 12 is used to form the first ETL. The compound E-01 in Formula 12 and Li (1 wt %) are used to form the n-type CGL, and the compound G-01 in Formula 12 and the compound in Formula 7 (10 wt %) are used to form the p-type CGL. In addition, the compound G-01 in Formula 12 is used to form the second HTL.

(2) Comparative Example 2 (Ref2)

The compound E-01 in Formula 12 is used to form the HBL, the compound F-02 in Formula 12 is used to form the first ETL. The compound E-01 in Formula 12 and Li (1 wt %) are used to form the n-type CGL, and the compound G-01 in Formula 12 and the compound in Formula 7 (10 wt %) are used to form the p-type CGL. In addition, the compound G-02 in Formula 12 is used to form the second HTL.

2. Example (1) Example 1 (Ex1)

The compound A-01 in Formula 2 is used to form the HBL, the compound A-02 in Formula 2 is used to form the first ETL. The compound B-03 in Formula 4 and Li (1 wt %) are used to form the n-type CGL, and the compound C-01 in Formula 6 and the compound in Formula 7 (10 wt %) are used to form the p-type CGL. In addition, the compound C-01 in Formula 6 is used to form the second HTL.

(2) Example 2 (Ex2)

The compound A-01 in Formula 2 is used to form the HBL, the compound A-01 in Formula 2 is used to form the first ETL. The compound B-05 in Formula 4 and Li (1 wt %) are used to form the n-type CGL, and the compound C-03 in Formula 6 and the compound in Formula 7 (10 wt %) are used to form the p-type CGL. In addition, the compound C-02 in Formula 6 is used to form the second HTL.

(3) Example 3 (Ex3)

The compound A-03 in Formula 2 is used to form the HBL, the compound A-02 in Formula 2 is used to form the first ETL. The compound B-06 in Formula 4 and Cs (1 wt %) are used to form the n-type CGL, and the compound C-04 in Formula 6 and the compound in Formula 7 (10 wt %) are used to form the p-type CGL. In addition, the compound C-02 in Formula 6 is used to form the second HTL.

(4) Example 4 (Ex4)

The compound A-04 in Formula 2 is used to form the HBL, the compound A-04 in Formula 2 is used to form the first ETL. The compound B-06 in Formula 4 and Li (1 wt %) are used to form the n-type CGL, and the compound C-01 in Formula 6 and the compound in Formula 7 (10 wt %) are used to form the p-type CGL. In addition, the compound C-02 in Formula 6 is used to form the second HTL.

(5) Example 5 (Ex5)

The compound A-05 in Formula 2 is used to form the HBL, the compound A-02 in Formula 2 is used to form the first ETL. The compound B-08 in Formula 4 and Li (1 wt %) are used to form the n-type CGL, and the compound C-05 in Formula 6 and the compound in Formula 7 (10 wt %) are used to form the p-type CGL. In addition, the compound C-01 in Formula 6 is used to form the second HTL.

(6) Example 6 (Ex6)

The compound A-05 in Formula 2 is used to form the HBL, the compound A-01 in Formula 2 is used to form the first ETL. The compound B-14 in Formula 4 and Li (1 wt %) are used to form the n-type CGL, and the compound C-07 in Formula 6 and the compound in Formula 7 (10 wt %) are used to form the p-type CGL. In addition, the compound C-02 in Formula 6 is used to form the second HTL.

(7) Example 7 (Ex7)

The compound A-06 in Formula 2 is used to form the HBL, the compound A-02 in Formula 2 is used to form the first ETL. The compound B-16 in Formula 4 and Li (1 wt %) are used to form the n-type CGL, and the compound C-07 in Formula 6 and the compound in Formula 7 (10 wt %) are used to form the p-type CGL. In addition, the compound C-02 in Formula 6 is used to form the second HTL.

(8) Example 8 (Ex8)

The compound A-07 in Formula 2 is used to form the HBL, the compound A-01 in Formula 2 is used to form the first ETL. The compound B-19 in Formula 4 and Li (1 wt %) are used to form the n-type CGL, and the compound C-09 in Formula 6 and the compound in Formula 7 (10 wt %) are used to form the p-type CGL. In addition, the compound C-02 in Formula 6 is used to form the second HTL.

(9) Example 9 (Ex9)

The compound A-08 in Formula 2 is used to form the HBL, the compound A-04 in Formula 2 is used to form the first ETL. The compound B-20 in Formula 4 and Li (1 wt %) are used to form the n-type CGL, and the compound C-10 in Formula 6 and the compound in Formula 7 (10 wt %) are used to form the p-type CGL. In addition, the compound C-01 in Formula 6 is used to form the second HTL.

[Formula 12]

E-01

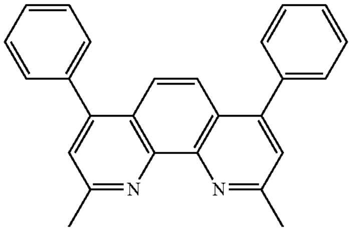

F-01

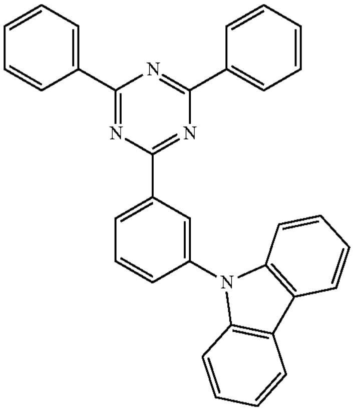

F-02

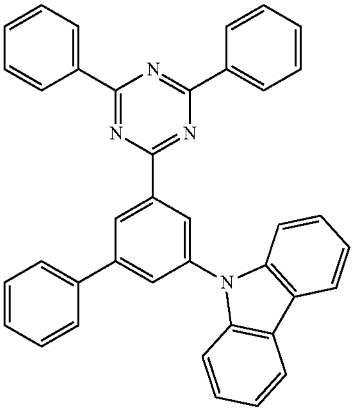

G-01

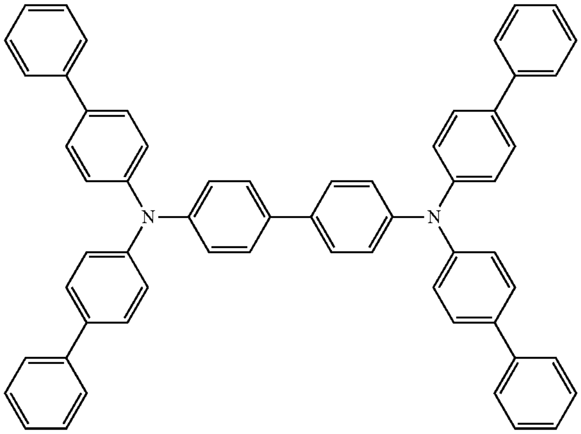

-continued

G-02

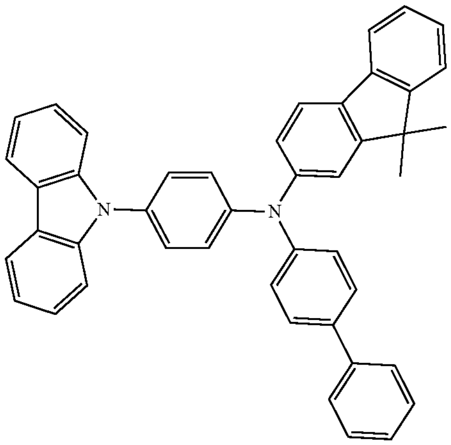

The HOMO energy level and the LUMO energy level of the compounds used in Comparative Examples 1 and 2 and Examples 1 to 9 are measured and listed in Table 1.

1) An organic material is deposited with 500 Å on an ITO glass by a vacuum deposition, and the HOMO level of the organic material is measured by using AC3 measurement apparatus.

2) The organic material (0.1 g) is dissolved in a mixed solution (1 L) of toluene and dichloromethane, and an energy band gap of the organic material is measured. The LUMO energy level is calculated from the HOMO energy level and the energy band gap.

The driving voltage of the OLED of Ref1, Ref2 and Ex1 to Ex9 are measured and listed in Table 2. ("V(@10 A/$m^2$)" is a driving voltage at a current density of 10 A/$m^2$, and "V(@T50)" is a driving voltage at a luminance of 50% with respect to an initial luminance.

TABLE 1

| | 1st compound | | | 2nd compound | | | 3rd compound | |
|---|---|---|---|---|---|---|---|---|
| | HOMO | LUMO | | HOMO | LUMO | | HOMO | LUMO |
| E-01 | 6.2 | 3.1 | B-03 | 6.0 | 3.3 | G-01 | 5.8 | 2.1 |
| F-01 | 6.3 | 3.2 | B-05 | 5.9 | 3.1 | G-02 | 5.9 | 2.0 |
| F-02 | 6.3 | 3.3 | B-06 | 6.0 | 3.3 | C-01 | 5.5 | 1.6 |
| A-01 | 5.6 | 2.8 | B-08 | 5.9 | 3.2 | C-02 | 5.4 | 1.5 |
| A-02 | 5.7 | 2.8 | B-14 | 6.0 | 3.2 | C-03 | 5.4 | 1.4 |
| A-03 | 5.6 | 2.7 | B-16 | 6.0 | 3.2 | C-04 | 5.3 | 1.5 |
| A-04 | 5.7 | 2.8 | B-19 | 6.1 | 3.1 | C-05 | 5.3 | 1.4 |
| A-05 | 5.7 | 2.8 | B-20 | 6.0 | 3.1 | C-07 | 5.2 | 1.5 |
| A-06 | 5.7 | 2.7 | | | | C-09 | 5.2 | 1.3 |
| A-07 | 5.6 | 2.6 | | | | C-010 | 5.3 | 1.3 |
| A-08 | 5.7 | 2.7 | | | | PD-01 | — | 5.07 |

TABLE 2

| | HBL | ETL1 | NCGL | PCGL | HTL2 | V (@10 A/$m^2$) | V (@T50) |
|---|---|---|---|---|---|---|---|
| Ref1 | E-01 | F-01 | E-01 | G-01 | G-01 | 6.8 V | 7.9 V |
| Ref2 | E-01 | F-02 | E-01 | G-01 | G-02 | 6.9 V | 7.9 V |
| Ex1 | A-G1 | A-02 | B-03 | C-01 | C-01 | 6.5 V | 7.1 V |
| Ex2 | A-01 | A-01 | B-05 | C-03 | C-02 | 6.6 V | 6.7 V |
| Ex3 | A-03 | A-02 | B-06 | C-04 | C-02 | 6.4 V | 7.1 V |
| Ex4 | A-04 | A-04 | B-06 | C-01 | C-02 | 6.8 V | 6.7 V |
| Ex5 | A-05 | A-02 | B-08 | C-05 | C-01 | 6.7 V | 7.1 V |
| Ex6 | A-05 | A-01 | B-14 | C-07 | C-02 | 6.1 V | 7.1 V |
| Ex7 | A-06 | A-02 | B-16 | C-07 | C-02 | 6.5 V | 6.7 V |

TABLE 2-continued

| | HBL | ETL1 | NCGL | PCGL | HTL2 | V (@10 A/$m^2$) | V (@T50) |
|---|---|---|---|---|---|---|---|
| Ex8 | A-07 | A-01 | B-19 | C-09 | C-02 | 5.6 V | 7.1 V |
| Ex9 | A-08 | A-04 | B-20 | C-10 | C-01 | 6.6 V | 7.1 V |

As shown in Tables 1 and 2, in comparison to the OLED of Ref1 and Ref2, the driving voltage of the OLED of Ex1 to Ex9 is decreased.

In the OLED of Ref1 and Ref2, the LUMO energy level of the material, i.e., the compound F-01 or the compound F-02, in the first ETL is not higher than that of the host, i.e., the compound E-01, in the n-type CGL so that the driving voltage is increased.

However, in the OLED of Ex1 to Ex9, the LUMO energy level of the material in the first ETL is higher than that of the host in the n-type CGL so that the driving voltage is decreased.

In addition, in the OLED of Ex2, Ex4 and Ex7, the increase of the driving voltage according to the operation of the OLED is significantly decreased, and the durability of the OLED is improved.

It will be apparent to those skilled in the art that various modifications and variations can be made in the present disclosure without departing from the spirit or scope of the present disclosure. Thus, it is intended that the present disclosure cover the modifications and variations of this disclosure provided they come within the scope of the appended claims and their equivalents.

What is claimed is:

1. An organic light emitting diode, comprising:

a first electrode;

a second electrode facing the first electrode;

a first emitting part including a first emitting material layer and a first electron transporting layer and positioned between the first electrode and the second electrode;

a second emitting part including a second emitting material layer and positioned between the first emitting part and the second electrode;

an n-type charge generation layer contacting the first electron transporting layer and positioned between the first electron transporting layer and the second emitting part; and a p-type charge generation layer contacting the n-type charge generation layer and positioned between the n-type charge generation layer and the second emitting part, wherein the first electron transporting layer includes a first compound, and the n-type charge generation layer includes a second compound and an n-type dopant, wherein a lowest unoccupied molecular orbital (LUMO) energy level of the first compound is higher than a LUMO energy level of the second compound, and a difference between the LUMO energy level of the first compound and the LUMO energy level of the second compound is about 0.3 to 1.0 eV, wherein the first compound is represented by Formula 1:

[Formula 1]

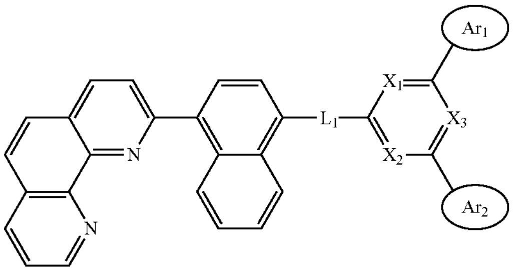

, wherein each of $X_1$, $X_2$ and $X_3$ is independently N or CR, and at least one of $X_1$, $X_2$ and $X_3$ is N, wherein R is selected from the group consisting of hydrogen, a substituted or unsubstituted C1 to C10 alkyl group, a substituted or unsubstituted C6 to C30 aryl group and a substituted or unsubstituted C3 to C30 heteroaryl group, wherein $L_1$ is a substituted or unsubstituted C6 to C30 arylene group, and a is 0 or 1, and wherein each of $Ar_1$ and $Ar_2$ is independently selected from the group consisting of a substituted or unsubstituted C6 to C30 aryl group and a substituted or unsubstituted C3 to C30 heteroaryl group, wherein the second compound is represented by Formula 3:

[Formula 3]

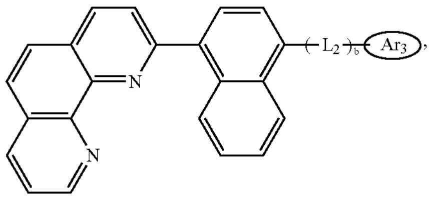

wherein $L_2$ is a substituted or unsubstituted C6 to C30 arylene group, and b is 0 or 1, and wherein $Ar_3$ is selected from the group consisting of a substituted or unsubstituted C6 to C30 aryl group and a substituted or unsubstituted C3 to C30 heteroaryl group containing at least one of O and S.

2. The organic light emitting diode according to claim 1, wherein the first compound is represented by Formula 2:

[Formula 2]

A-01

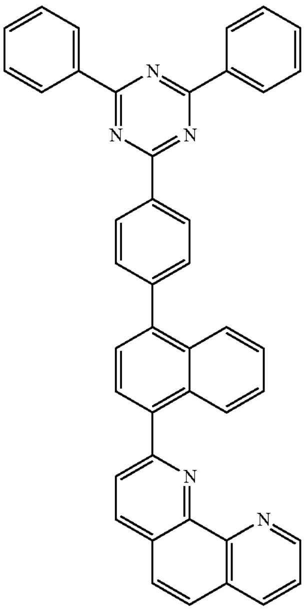

A-02

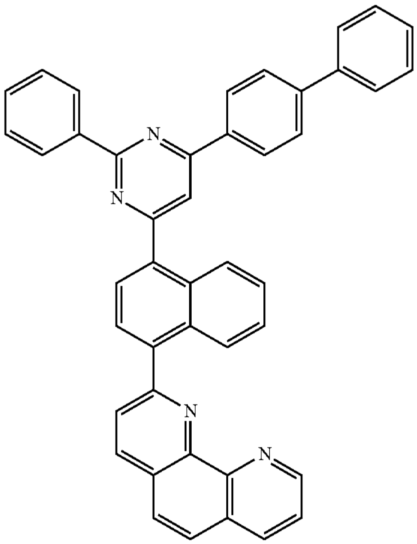

-continued
A-03
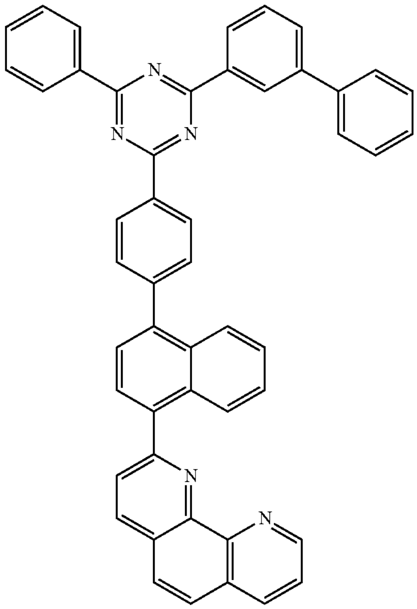
A-04
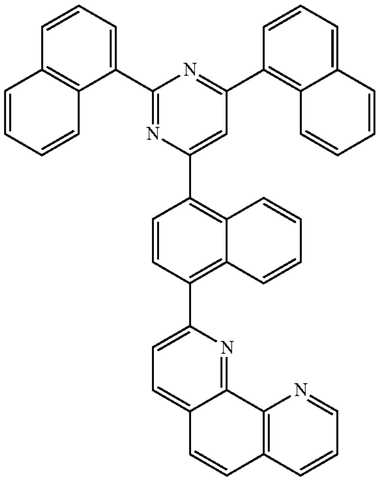
-continued
A-05
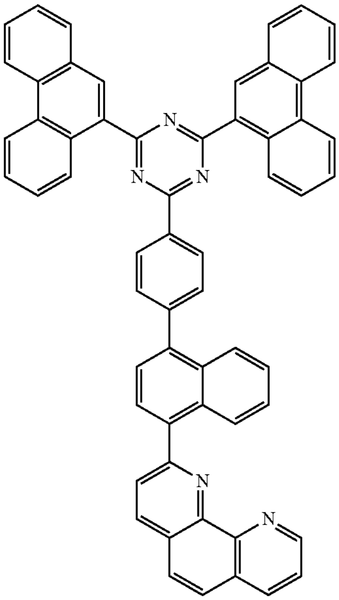
A-06
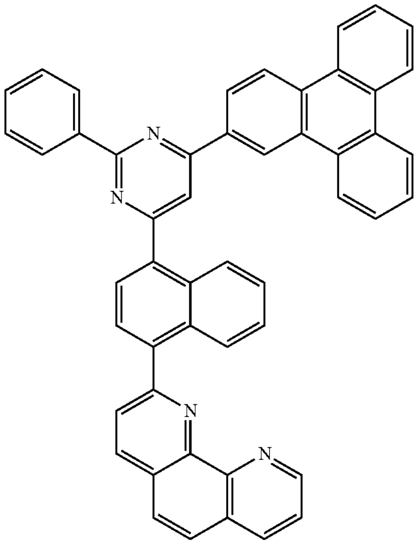

-continued
A-07
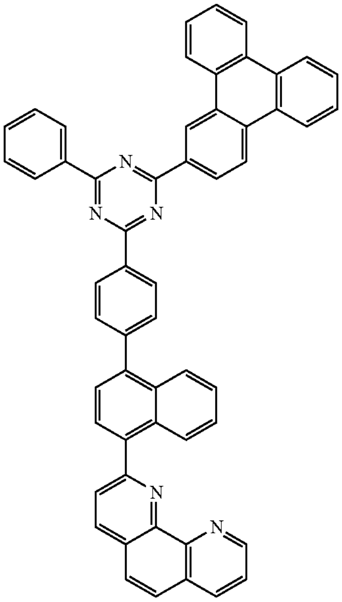
A-08
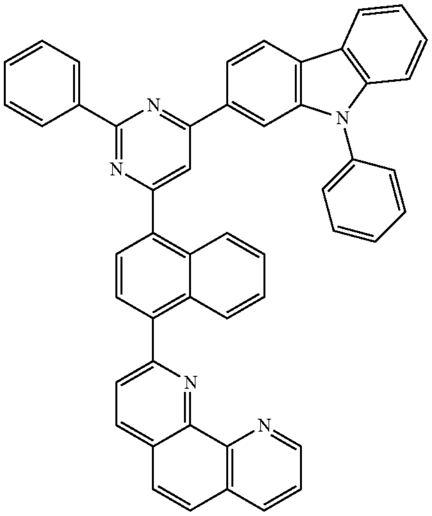
-continued
A-09
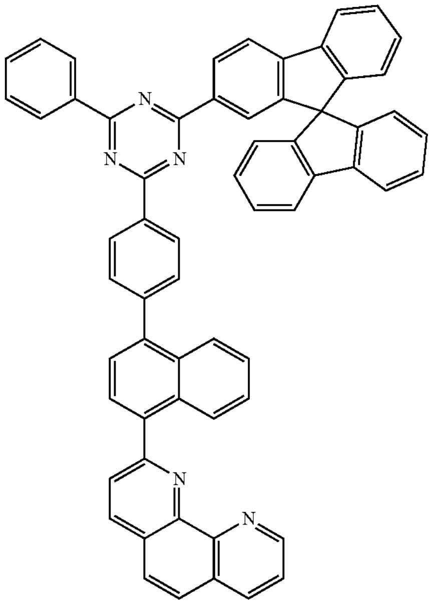
A-10
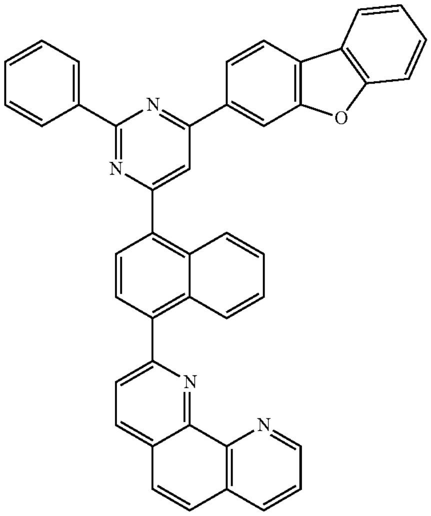
3. The organic light emitting diode according to claim 1, wherein the second compound is one of compounds in Formula 4:

[Formula 4]
B-01
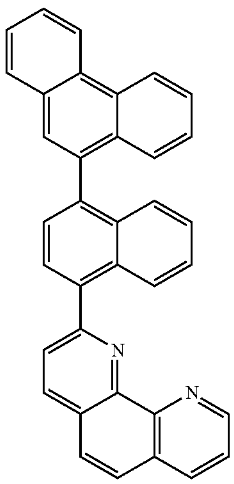
B-02
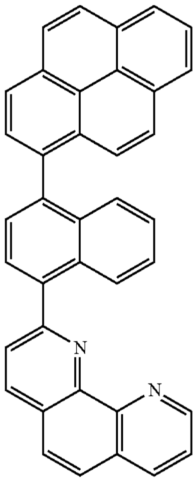
B-03
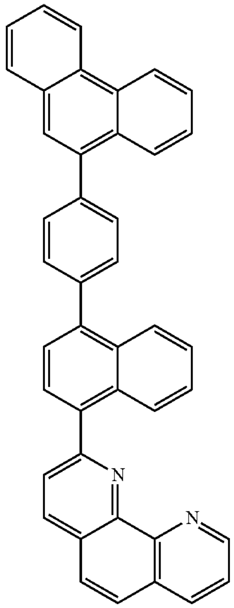
-continued
B-04
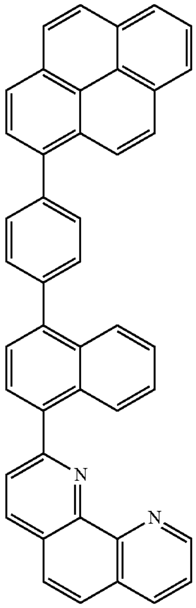
B-05
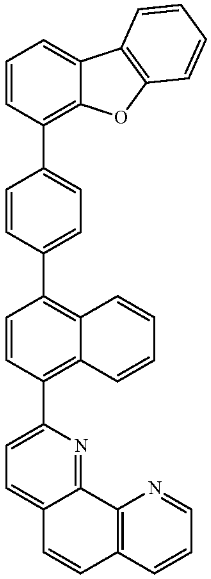
B-06
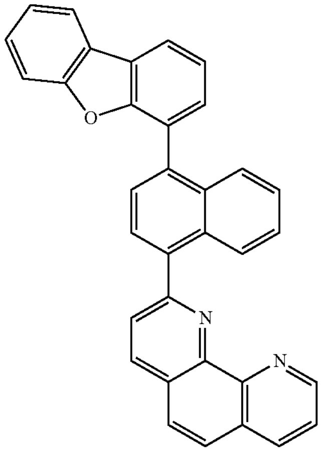

B-07
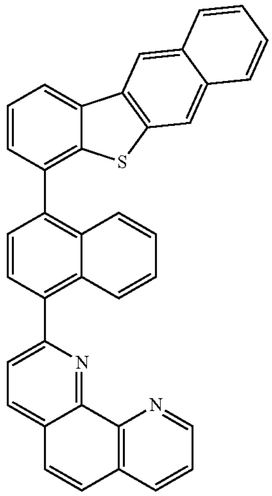
B-08
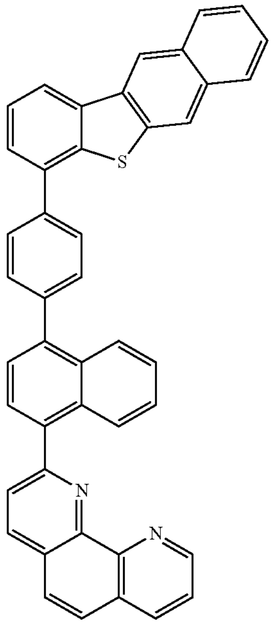
B-09
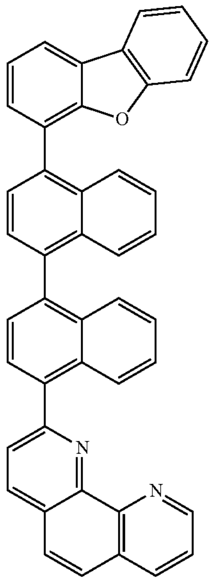
B-10
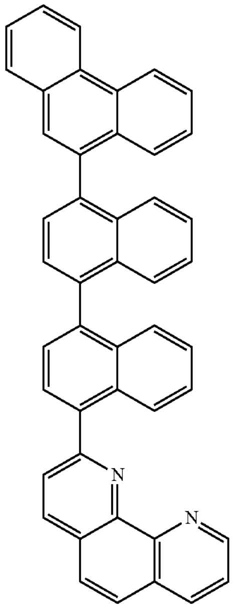

-continued
B-11
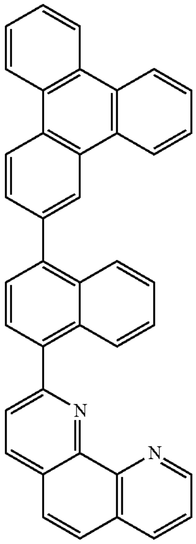
B-12
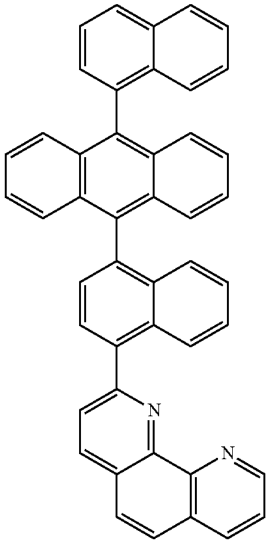
-continued
B-13
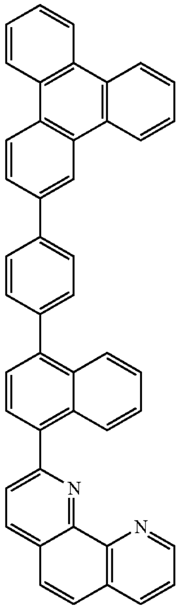
B-14
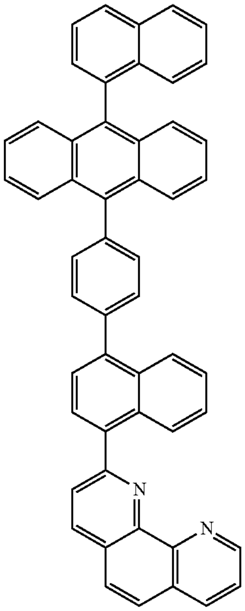

-continued
B-15
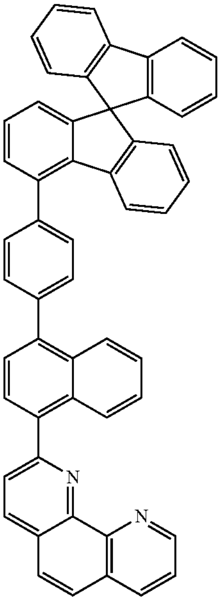
B-16
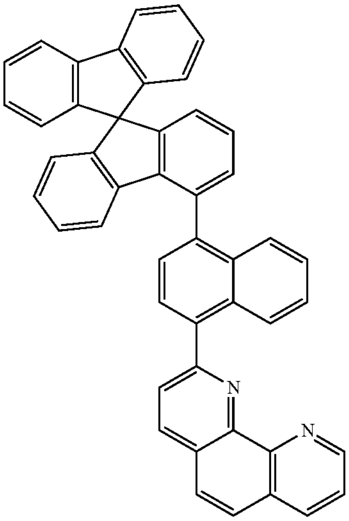
-continued
B-17
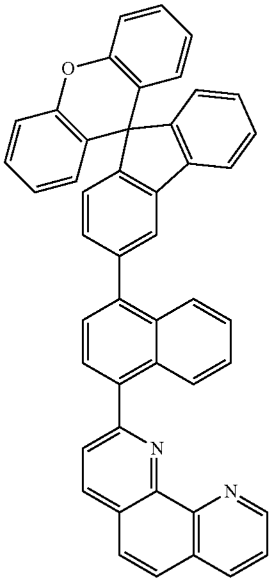
B-18
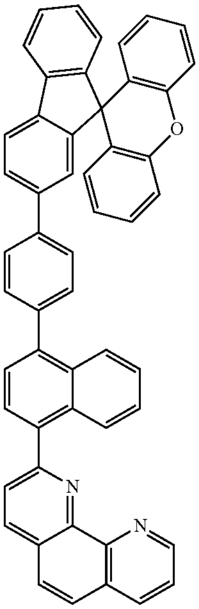

-continued

B-19

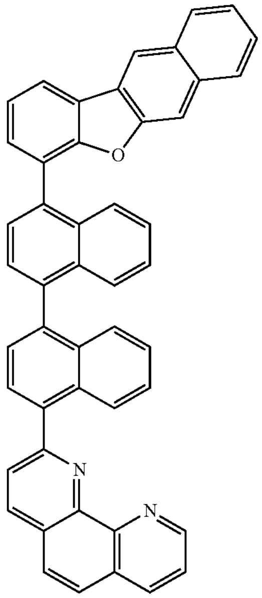

B-20

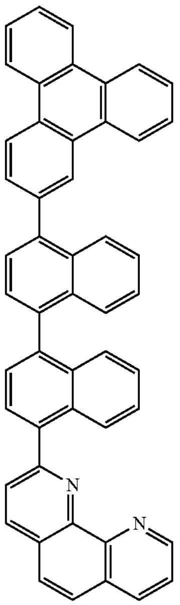

4. The organic light emitting diode according to claim 1, wherein the n-type dopant is Li or Cs.

5. The organic light emitting diode according to claim 1, wherein the p-type charge generation layer includes a third compound and a p-type dopant, and wherein a LUMO energy level of the third compound is higher than the LUMO energy level of the second compound.

6. The organic light emitting diode according to claim 5, wherein a difference between the LUMO energy level of the third compound and the LUMO energy level of the second compound is about 1.0 to 2.0 eV.

7. The organic light emitting diode according to claim 5, wherein the third compound is represented by Formula 5:

[Formula 5]

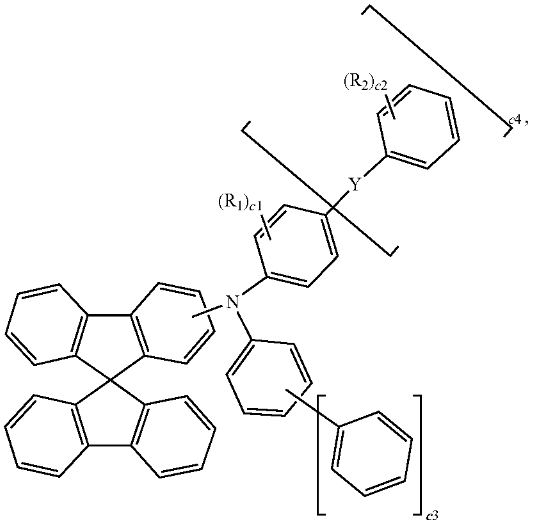

wherein each of $R_1$ and $R_2$ is independently selected from the group consisting of a substituted or unsubstituted C1 to C10 alkyl group and a substituted or unsubstituted C6 to C30 aryl group, or $R_1$ and $R_2$ are connected to form a ring, wherein Y is a single bond (direct bond) or $NR_3$, and $R_3$ is selected from the group consisting of hydrogen, a substituted or unsubstituted C1 to C10 alkyl group and a substituted or unsubstituted C6 to C30 aryl group, and wherein $c_1$ is an integer of 0 to 4, $c_2$ is an integer of 0 to 5, and each of $c_3$ and $c_4$ is independently 0 or 1.

8. The organic light emitting diode according to claim 7, wherein the third compound is one of compounds in Formula 6:

[Formula 6]

C-01

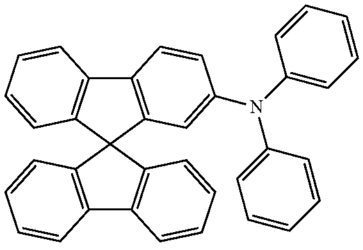

-continued
C-02
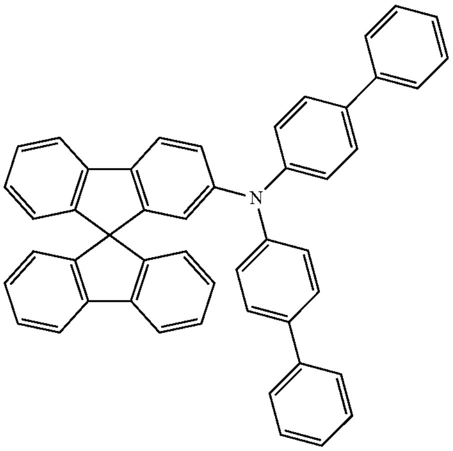
C-03
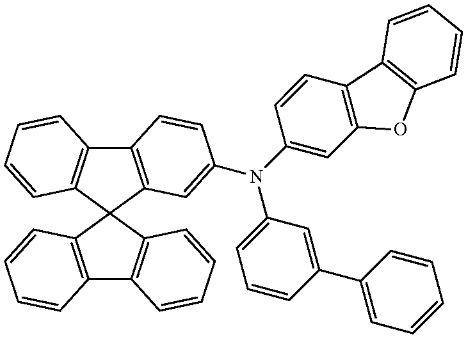
C-04
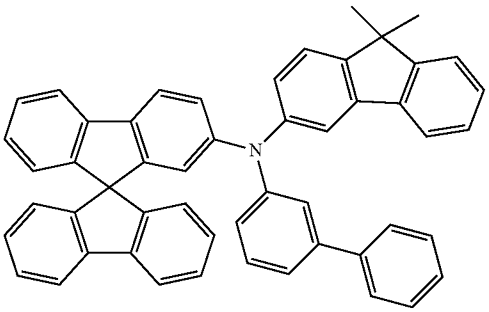
C-05
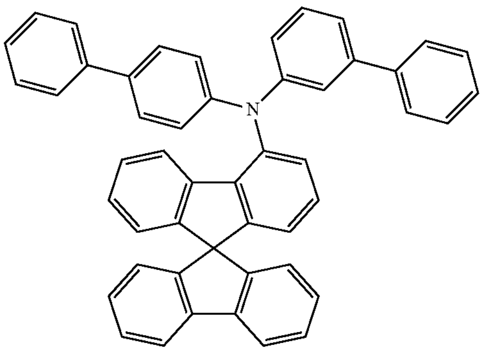
-continued
C-06
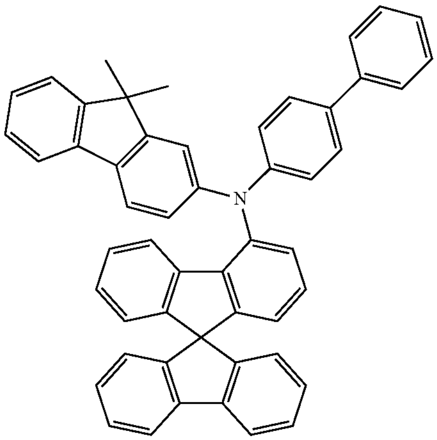
C-07
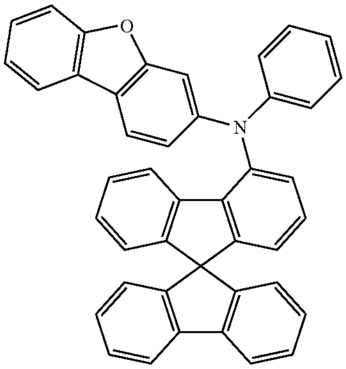
C-08
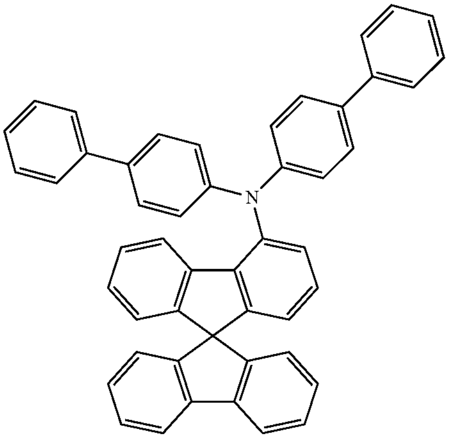

-continued

C-09

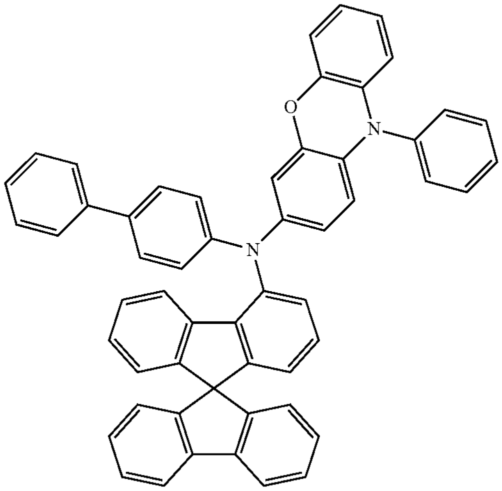

C-10

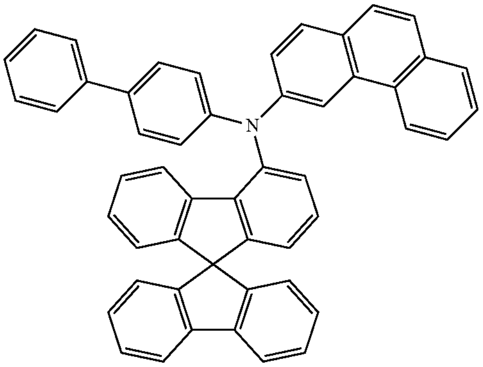

9. The organic light emitting diode according to claim 5, wherein a LUMO energy level of the p-type dopant is higher than a HOMO energy level of the third compound, and a difference between the LUMO energy level of the p-type dopant and the HOMO energy level of the third compound is 0.1 to 0.5 eV.

10. The organic light emitting diode according to claim 9, wherein the p-type dopant is a compound in Formula 7:

[Formula 7]

PD-01

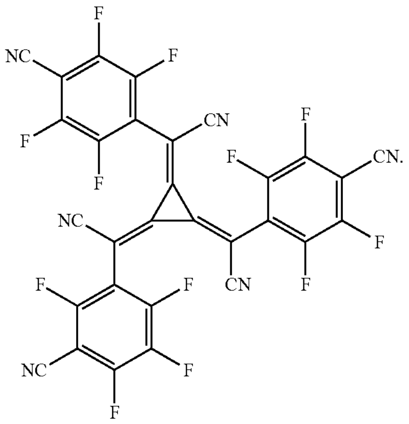

11. The organic light emitting diode according to claim 1, wherein the first emitting part further includes a hole blocking layer contacting the first electron transporting layer and positioned between the first emitting material layer and the first electron transporting layer, and wherein the hole blocking layer includes a hole blocking material represented by Formula 1.

12. The organic light emitting diode according to claim 11, wherein the first compound and the hole blocking material are same or different.

13. The organic light emitting diode according to claim 7, wherein the second emitting part further includes a hole transporting layer positioned under the second emitting material layer and contacting the p-type charge generation layer, and wherein the hole transporting layer includes a hole transporting material represented by Formula 5.

14. The organic light emitting diode according to claim 13, wherein the third compound and the hole transporting material are same or different.

15. The organic light emitting diode according to claim 13, wherein a difference between a LUMO energy level of the hole transporting material and the LUMO energy level of the third compound is 0 to about 0.2 eV.

16. An organic light emitting display device, comprising:

a substrate including a red pixel region, a green pixel region and a blue pixel region; and an organic light emitting diodes positioned over the substrate and corresponding to at least one of the red pixel region, the green pixel region and the blue pixel region, the organic light emitting diode including:

a first electrode;

a second electrode facing the first electrode;

a first emitting part including a first emitting material layer and a first electron transporting layer and positioned between the first electrode and the second electrode;

a second emitting part including a second emitting material layer and positioned between the first emitting part and the second electrode;

an n-type charge generation layer contacting the first electron transporting layer and positioned between the first electron transporting layer and the second emitting part; and a p-type charge generation layer contacting the n-type charge generation layer and positioned between the n-type charge generation layer and the second emitting part, wherein the first electron transporting layer includes a first compound, and the n-type charge generation layer includes a second compound and an n-type dopant, wherein a lowest unoccupied molecular orbital (LUMO) energy level of the first compound is higher than a LUMO energy level of the second compound, and a difference between the LUMO energy level of the first compound and the LUMO energy level of the second compound is about 0.3 to 1.0 eV, wherein the first compound is represented by Formula 1:

[Formula 1]

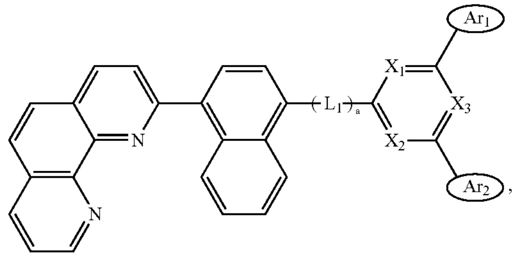

wherein each of $X_1$, $X_2$ and $X_3$ is independently N or CR, and at least one of $X_1$, $X_2$ and $X_3$ is N, wherein R is selected from the group consisting of hydrogen, a substituted or unsubstituted C1 to C10 alkyl group, a substituted or unsubstituted C6 to C30 aryl group and a substituted or unsubstituted C3 to C30 heteroaryl group, wherein $L_1$ is a substituted or unsubstituted C6 to C30 arylene group, and a is 0 or 1, and wherein each of $Ar_1$ and $Ar_2$ is independently selected from the group consisting of a substituted or unsubstituted C6 to C30 aryl group and a substituted or unsubstituted C3 to C30 heteroaryl group, wherein the second compound is represented by Formula 3:

[Formula 3]

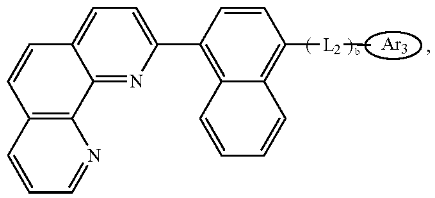

wherein $L_2$ is a substituted or unsubstituted C6 to C30 arylene group, and b is 0 or 1, and wherein $Ar_3$ is selected from the group consisting of a substituted or unsubstituted C6 to C30 aryl group and a substituted or unsubstituted C3 to C30 heteroaryl group containing at least one of O and S.

17. The organic light emitting diode according to claim 1, wherein the first emitting material layer includes a first host and a first dopant, and the second emitting material layer includes a second host and a second dopant, and wherein each of the first host and the second host is a compound in Formula 10, and each of the first dopant and the second dopant is a compound in Formula 11:

[Formula 10]

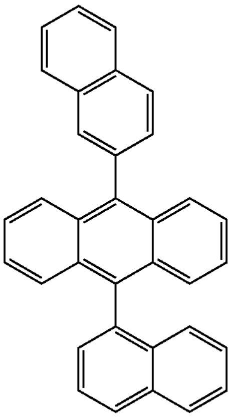

[Formula 11]

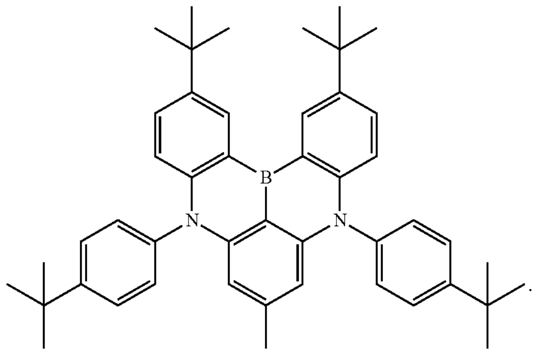

18. An organic light emitting display device according to claim 16, wherein the first emitting material layer includes a first host and a first dopant, and the second emitting material layer includes a second host and a second dopant, and wherein each of the first host and the second host is a compound in Formula 10, and each of the first dopant and the second dopant is a compound in Formula 11:

[Formula 10]

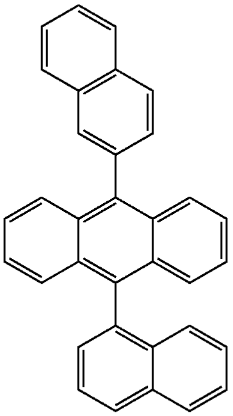

-continued
[Formula 11]
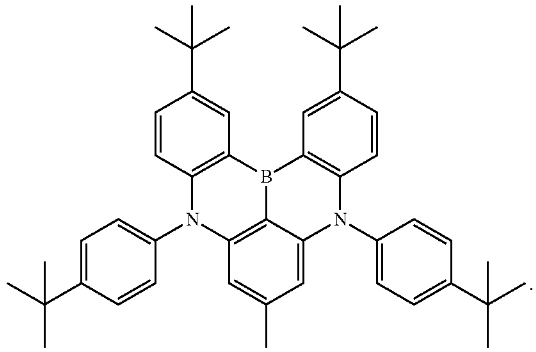
.
* * * * *